(12) United States Patent
Pinzon et al.

(10) Patent No.: US 7,276,547 B2
(45) Date of Patent: *Oct. 2, 2007

(54) COMPOSITIONS COMPRISING HETEROPOLYMERS AND AT LEAST ONE OIL-SOLUBLE POLYMERS CHOSEN FROM ALKYL CELLULOSES AND ALKYLATED GUAR GUMS

(75) Inventors: Carlos Pinzon, New Milford, NJ (US); Paul Thau, Berkeley Heights, NJ (US)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/733,896

(22) Filed: Dec. 12, 2000

(65) Prior Publication Data

US 2003/0125427 A9  Jul. 3, 2003

(51) Int. Cl.
 *A61K 8/31* (2006.01)
 *A61K 8/42* (2006.01)
 *A61K 8/73* (2006.01)
 *A61K 8/88* (2006.01)
(52) U.S. Cl. .......................... 524/46; 532/55
(58) Field of Classification Search ................ 524/35, 524/37, 38, 39, 43, 44, 45, 46, 55
 See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway ............ 167/85 |
| 3,141,787 A | 7/1964 | Goetze et al. |
| 3,148,125 A | 9/1964 | Strianse et al. ........ 167/85 |
| 3,156,572 A | 11/1964 | Carlick et al. |
| 3,157,681 A | 11/1964 | Fischer |
| 3,255,082 A | 6/1966 | Barton |
| 3,324,041 A | 6/1967 | Sommer et al. |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. ............ 44/7.5 |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. ........ 424/70 |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,367,390 A | 1/1983 | Balleys et al. |
| 4,376,194 A | 3/1983 | Tanaka et al. |
| 4,387,090 A | 6/1983 | Bolich, Jr. ............. 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ........ 252/522 |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A * | 10/1987 | Palinczar ............... 424/59 |
| 4,712,571 A | 12/1987 | Remz et al. |

(Continued)

FOREIGN PATENT DOCUMENTS

CA       1319306       6/1988

(Continued)

OTHER PUBLICATIONS

Kenji Hanabusa et al., *Terephthaloyl Derivatives as New Gelators; Excellent Gelation Ability and Remarkable Increase of Gel Strength by Adding Polymers*, 1999 Chemistry Letters 767.

Xuzhong Luo et al., *Self-assembled organogels formed by monoalkyl derivatives of oxamide*, 2000 Chem. Commun. 2091-92.

Kenji Hanabusa et al., *Easy Preparation and Gelation of New Gelator Based on L-Lysine*, 2000 Chemistry Letters, 1070.

Co-Pending U.S. Appl. No. 09/749,036; Title: Composition Comprising at Least One Hetero Polymer and at Least One Pasty Fatty Substance and Methods for Use Inventors: Véronique Ferrari et al. filed Dec. 28, 2000.

PCT Application No. PCT/US01/47459; Title: Cosmetic Compositions Containing at Least One Heteropolymer and at Least One Film-Forming Silicone Resin and Methods of Using Inventors: Mohamed Kanji et al. filed Dec. 12, 2001.

(Continued)

*Primary Examiner*—Nathan M. Nutter
(74) *Attorney, Agent, or Firm*—Finnegan, Henderson, Farabow, Garrett & Dunner, L.L.P.

(57) ABSTRACT

Compositions comprising at least one structuring polymer and at least one oil-soluble polymer chosen from alkyl celluloses and alkylated guar gums. The compositions may further comprise at least one fatty alcohol. This composition may be in the form of stable compositions such as, for example, make-up sticks, lipsticks and sunscreen sticks.

16 Claims, No Drawings

U.S. PATENT DOCUMENTS

| | | | |
|---|---|---|---|
| 4,724,137 A | 2/1988 | Hoppe et al. | |
| 4,769,285 A | 9/1988 | Rasmussen | |
| 4,806,338 A | 2/1989 | Smith | 424/47 |
| 4,806,345 A | 2/1989 | Bhattacharyya | 424/70 |
| 4,820,765 A | 4/1989 | Whyzmuzis | |
| 4,822,601 A | 4/1989 | Goode et al. | |
| 4,871,536 A | 10/1989 | Arraudeau et al. | 424/59 |
| 4,885,709 A | 12/1989 | Edgar et al. | |
| 4,937,069 A | 6/1990 | Shin | |
| 4,952,245 A | 8/1990 | Iwano et al. | |
| 5,034,219 A | 7/1991 | Deshpande et al. | |
| 5,061,289 A | 10/1991 | Clausen et al. | |
| 5,069,897 A | 12/1991 | Orr | 424/66 |
| 5,073,364 A | 12/1991 | Giezendanner et al. | |
| 5,085,859 A | 2/1992 | Halloran et al. | |
| 5,102,656 A | 4/1992 | Kasat | |
| 5,166,355 A | 11/1992 | Leistner et al. | |
| 5,186,318 A | 2/1993 | Oestreich et al. | 206/37 |
| 5,196,260 A | 3/1993 | Dirschl et al. | |
| 5,223,559 A | 6/1993 | Arraudeau et al. | |
| 5,237,071 A | 8/1993 | Leistner et al. | |
| 5,252,323 A | 10/1993 | Richard et al. | |
| 5,268,029 A | 12/1993 | Demangeon et al. | |
| 5,272,241 A | 12/1993 | Lucarelli et al. | 528/15 |
| 5,290,555 A | 3/1994 | Guthauser et al. | |
| 5,302,378 A * | 4/1994 | Crotty et al. | 424/59 |
| 5,302,398 A | 4/1994 | Egidio et al. | |
| 5,342,894 A | 8/1994 | Robeson et al. | |
| 5,362,482 A | 11/1994 | Yoneyama et al. | |
| 5,372,852 A | 12/1994 | Titterington et al. | |
| 5,389,363 A | 2/1995 | Snyder et al. | |
| 5,436,006 A | 7/1995 | Hirose et al. | |
| 5,472,686 A | 12/1995 | Tsubaki et al. | |
| 5,486,431 A | 1/1996 | Tuttle et al. | |
| 5,489,431 A | 2/1996 | Ascione et al. | |
| 5,500,209 A * | 3/1996 | Mendolia et al. | 424/66 |
| 5,505,937 A | 4/1996 | Castrogiovanni et al. | |
| 5,510,452 A | 4/1996 | Santhanam | 528/291 |
| 5,536,871 A | 7/1996 | Santhanam | 560/196 |
| 5,538,718 A | 7/1996 | Aul et al. | |
| 5,538,793 A | 7/1996 | Inokuchi et al. | |
| 5,540,853 A | 7/1996 | Trinh et al. | 510/101 |
| 5,585,091 A | 12/1996 | Pelzer et al. | |
| 5,603,925 A | 2/1997 | Ross et al. | 424/65 |
| 5,605,651 A | 2/1997 | Balzer | |
| 5,610,199 A | 3/1997 | Cohen et al. | |
| 5,612,043 A | 3/1997 | Deprez et al. | |
| 5,616,331 A | 4/1997 | Allard et al. | |
| 5,618,523 A | 4/1997 | Zysman et al. | 424/70.1 |
| 5,620,693 A | 4/1997 | Piot et al. | |
| 5,645,632 A | 7/1997 | Pavlin | |
| 5,667,770 A | 9/1997 | Szweda et al. | 424/64 |
| 5,679,357 A | 10/1997 | Dubief et al. | 424/401 |
| 5,683,817 A | 11/1997 | Kenmochi | |
| 5,695,747 A | 12/1997 | Forestier et al. | |
| 5,702,519 A | 12/1997 | Nitta et al. | |
| 5,719,255 A | 2/1998 | Heucher et al. | |
| 5,747,625 A | 5/1998 | Furukawa et al. | |
| 5,750,125 A | 5/1998 | Lahanas et al. | |
| 5,750,127 A | 5/1998 | Rokitowski | |
| 5,750,489 A | 5/1998 | Garcia et al. | |
| 5,769,902 A | 6/1998 | Samain | |
| 5,780,517 A | 7/1998 | Cohen et al. | |
| 5,783,657 A * | 7/1998 | Pavlin et al. | 528/310 |
| 5,795,565 A | 8/1998 | Eteve et al. | |
| 5,800,816 A | 9/1998 | Brieva et al. | 424/63 |
| 5,807,968 A | 9/1998 | Heinrich et al. | |
| 5,830,444 A | 11/1998 | Miguel | |
| 5,830,483 A | 11/1998 | Seidel et al. | |
| 5,837,223 A | 11/1998 | Barone et al. | |
| 5,849,275 A | 12/1998 | Calello et al. | |
| 5,849,278 A | 12/1998 | Piot et al. | |
| 5,849,333 A | 12/1998 | Nordhauser et al. | |
| 5,849,909 A | 12/1998 | Richard et al. | |
| 5,851,517 A | 12/1998 | Mougin et al. | |
| 5,857,903 A | 1/1999 | Ramspeck et al. | |
| 5,858,338 A | 1/1999 | Piot et al. | |
| 5,866,149 A | 2/1999 | Piot et al. | |
| 5,871,764 A | 2/1999 | Diaz et al. | |
| 5,874,069 A | 2/1999 | Mendolia et al. | 424/65 |
| 5,882,363 A | 3/1999 | Spaulding et al. | |
| 5,891,424 A | 4/1999 | Bretzler et al. | |
| 5,897,869 A | 4/1999 | Roulier et al. | 424/401 |
| 5,902,592 A | 5/1999 | Bara et al. | |
| 5,908,631 A * | 6/1999 | Arnaud et al. | 424/401 |
| 5,911,974 A | 6/1999 | Brieva et al. | 424/64 |
| 5,919,441 A | 7/1999 | Mendolia et al. | 424/78.08 |
| 5,925,337 A | 7/1999 | Arraudeau et al. | |
| 5,945,095 A | 8/1999 | Mougin et al. | |
| 5,945,112 A | 8/1999 | Flynn et al. | |
| 5,955,060 A | 9/1999 | Huglin et al. | |
| 5,959,009 A | 9/1999 | Konik et al. | 524/261 |
| 5,961,998 A | 10/1999 | Arnaud et al. | |
| 5,962,452 A | 10/1999 | Haase et al. | |
| 5,965,112 A | 10/1999 | Brieva et al. | 424/64 |
| 5,972,095 A | 10/1999 | Graves et al. | |
| 5,972,354 A | 10/1999 | de la Poterie et al. | |
| 5,972,359 A | 10/1999 | Sine et al. | |
| 5,976,512 A | 11/1999 | Huber | |
| 5,976,514 A | 11/1999 | Guskey et al. | |
| 5,981,680 A | 11/1999 | Petroff et al. | |
| 5,985,298 A | 11/1999 | Brieva et al. | |
| 5,993,787 A | 11/1999 | Sun et al. | |
| 5,998,570 A | 12/1999 | Pavlin et al. | 528/310 |
| 6,001,980 A | 12/1999 | Borzo et al. | |
| 6,004,567 A | 12/1999 | Marchi-Lemann et al. | |
| 6,007,799 A | 12/1999 | Lee et al. | |
| 6,019,962 A | 2/2000 | Rabe et al. | |
| 6,036,947 A | 3/2000 | Barone et al. | |
| 6,045,782 A | 4/2000 | Krog et al. | |
| 6,045,823 A | 4/2000 | Vollhardt et al. | |
| 6,051,216 A | 4/2000 | Barr et al. | 424/78.35 |
| 6,054,517 A | 4/2000 | Spaulding et al. | |
| 6,060,072 A | 5/2000 | Konik et al. | 424/401 |
| 6,063,398 A | 5/2000 | Gueret | |
| 6,066,328 A | 5/2000 | Ribier et al. | |
| 6,074,654 A | 6/2000 | Drechsler et al. | 424/401 |
| 6,093,385 A | 7/2000 | Habeck et al. | |
| 6,103,249 A | 8/2000 | Roulier et al. | 424/401 |
| 6,106,820 A | 8/2000 | Morrissey et al. | |
| 6,111,055 A | 8/2000 | Berger et al. | |
| 6,132,745 A | 10/2000 | Marchi-Lemann et al. | |
| 6,156,325 A | 12/2000 | Farer et al. | 424/401 |
| 6,156,804 A | 12/2000 | Chevalier et al. | |
| 6,159,455 A | 12/2000 | Habeck et al. | |
| 6,165,454 A * | 12/2000 | Patel et al. | 424/70.11 |
| 6,165,971 A | 12/2000 | Oppenlander et al. | |
| 6,171,347 B1 | 1/2001 | Kunz et al. | |
| 6,177,523 B1 | 1/2001 | Reich et al. | 525/459 |
| 6,180,117 B1 | 1/2001 | Berthiaume et al. | |
| 6,180,123 B1 * | 1/2001 | Mondet | 424/401 |
| 6,190,673 B1 | 2/2001 | Guskey et al. | 424/401 |
| 6,197,100 B1 | 3/2001 | Melbouci | |
| 6,203,780 B1 | 3/2001 | Arnaud et al. | |
| 6,203,807 B1 | 3/2001 | Lemann | |
| 6,214,326 B1 | 4/2001 | Dupuis | |
| 6,214,329 B1 | 4/2001 | Brieva et al. | |
| 6,221,389 B1 | 4/2001 | Cannell et al. | |
| 6,224,851 B1 | 5/2001 | Bara | |
| 6,242,509 B1 | 6/2001 | Berger et al. | |
| 6,251,375 B1 | 6/2001 | Bara | |
| 6,251,409 B1 | 6/2001 | Hegyi et al. | |
| 6,254,876 B1 | 7/2001 | de la Poterie et al. | |
| 6,254,877 B1 | 7/2001 | de la Poterie et al. | |

| | | | | | | |
|---|---|---|---|---|---|---|
| 6,264,933 B1 | 7/2001 | Bodelin et al. | | 2004/0028636 A1 | 2/2004 | Collin |
| 6,268,466 B1 | 7/2001 | MacQueen et al. | | 2004/0042980 A1 | 3/2004 | Kanji et al. |
| 6,280,846 B1 | 8/2001 | Darby et al. | | 2004/0086478 A1 | 5/2004 | Ferrari |
| 6,287,552 B1 * | 9/2001 | Tournilhac et al. ...... 424/78.03 | | 2004/0091510 A1 | 5/2004 | Feng et al. |
| 6,325,994 B1 | 12/2001 | Collin et al. | | 2004/0126401 A1 | 7/2004 | Collin |
| 6,348,563 B1 | 2/2002 | Fukuda et al. | | 2004/0166076 A1 | 8/2004 | Ferrari et al. |
| 6,361,764 B2 | 3/2002 | Richard et al. | | 2004/0166133 A1 | 8/2004 | Cavazzuti et al. |
| 6,372,235 B1 | 4/2002 | Livoreil et al. | | 2004/0247549 A1 | 12/2004 | Lu et al. |
| 6,376,078 B1 | 4/2002 | Inokuchi | | 2005/0008598 A1 | 1/2005 | Lu et al. |
| 6,383,502 B1 | 5/2002 | Dunshee et al. | | 2005/0008599 A1 | 1/2005 | Lu et al. |
| 6,399,080 B1 | 6/2002 | Bara | | 2005/0065261 A1 | 3/2005 | Darlington, Jr. et al. |
| 6,399,081 B1 | 6/2002 | Nakanishi et al. | | 2005/0089491 A1 | 4/2005 | Collin |
| 6,402,408 B1 * | 6/2002 | Ferrari ................ 401/64 | | 2005/0089505 A1 | 4/2005 | Collin |
| 6,410,003 B1 | 6/2002 | Bhatia et al. | | 2005/0089541 A1 | 4/2005 | Lacoutiere |
| 6,423,306 B2 | 7/2002 | Caes et al. | | 2005/0191327 A1 | 9/2005 | Yu et al. |
| 6,423,324 B1 | 7/2002 | Murphy et al. | | 2005/0276767 A1 * | 12/2005 | Blin et al. ............ 424/63 |
| 6,428,773 B1 | 8/2002 | Oko et al. | | | | |
| 6,432,391 B1 | 8/2002 | Bara | | FOREIGN PATENT DOCUMENTS | | |
| 6,447,759 B2 | 9/2002 | Noguchi et al. | | CA | 2003346 | 5/1990 |
| 6,469,131 B2 | 10/2002 | Lawson et al. | | DE | 38 39 136 A1 | 5/1990 |
| 6,475,500 B2 | 11/2002 | Vatter et al. | | DE | 38 43 892 A | 6/1990 |
| 6,479,686 B2 | 11/2002 | Nakanishi et al. | | DE | 42 08 297 A | 9/1993 |
| 6,482,400 B1 | 11/2002 | Collin | | DE | 42 34 886 A | 4/1994 |
| 6,491,931 B1 | 12/2002 | Collin | | DE | 195 43 988 A | 5/1997 |
| 6,497,861 B1 | 12/2002 | Wang et al. | | DE | 197 07 309 A1 | 8/1998 |
| 6,503,522 B2 | 1/2003 | Lawson et al. | | DE | 197 26 184 A1 | 12/1998 |
| 6,506,716 B1 | 1/2003 | Delplancke et al. | | DE | 197 50 246 A1 | 5/1999 |
| 6,545,174 B2 | 4/2003 | Habeck et al. | | DE | 197 55 649 A1 | 6/1999 |
| 6,552,160 B2 | 4/2003 | Pavlin | | DE | 198 55 649 A1 | 6/2000 |
| 6,649,173 B1 | 11/2003 | Arnaud et al. | | DE | 199 51 010 | 4/2001 |
| 6,682,748 B1 | 1/2004 | De La Poterie et al. | | EP | 0 169 997 B1 | 2/1986 |
| 6,716,420 B2 * | 4/2004 | Feng et al. .......... 424/70.7 | | EP | 0 295 886 | 12/1988 |
| 6,726,917 B2 | 4/2004 | Kanji et al. | | EP | 0 370 470 B1 | 5/1990 |
| 6,761,881 B2 * | 7/2004 | Bara .................... 424/63 | | EP | 0 374 332 A1 | 6/1990 |
| 6,869,594 B2 | 3/2005 | Ferrari | | EP | 0 412 710 B1 | 2/1991 |
| 6,875,245 B2 | 4/2005 | Pavlin | | EP | 0 444 633 A2 | 9/1991 |
| 6,881,400 B2 | 4/2005 | Collin | | EP | 0 507 692 A1 | 10/1992 |
| 6,960,339 B1 | 11/2005 | Ferrari | | EP | 0 517 104 B1 | 12/1992 |
| 6,979,469 B2 | 12/2005 | Ferrari et al. | | EP | 0 518 772 A1 | 12/1992 |
| 2001/0014313 A1 | 8/2001 | Roulier et al. | | EP | 0 518 773 A1 | 12/1992 |
| 2001/0028887 A1 | 10/2001 | Douin et al. | | EP | 0 557 196 A1 | 8/1993 |
| 2001/0031280 A1 | 10/2001 | Ferrari et al. | | EP | 0 557 196 B1 | 8/1993 |
| 2001/0033846 A1 | 10/2001 | Roulier et al. | | EP | 0 570 838 B1 | 11/1993 |
| 2002/0010179 A1 | 1/2002 | Richard et al. | | EP | 0 602 905 B1 | 6/1994 |
| 2002/0044918 A1 | 4/2002 | Bara | | EP | 0 609 132 B1 | 8/1994 |
| 2002/0081323 A1 | 6/2002 | Nakanishi et al. | | EP | 0 623 670 A2 | 11/1994 |
| 2002/0102225 A1 | 8/2002 | Hess et al. | | EP | 0 628 582 B1 | 12/1994 |
| 2002/0107314 A1 | 8/2002 | Pinzon et al. | | EP | 0 669 323 A1 | 8/1995 |
| 2002/0111330 A1 | 8/2002 | Pinzon et al. | | EP | 0 673 642 B1 | 9/1995 |
| 2002/0114771 A1 | 8/2002 | Nakanishi et al. | | EP | 0 708 114 A1 | 4/1996 |
| 2002/0114773 A1 | 8/2002 | Kanji et al. | | EP | 0 749 746 A1 | 12/1996 |
| 2002/0119171 A1 | 8/2002 | Gruning et al. | | EP | 0 749 747 A1 | 12/1996 |
| 2002/0120036 A1 | 8/2002 | Pinzon et al. | | EP | 0 749 748 A | 12/1996 |
| 2002/0122781 A1 | 9/2002 | Pinzon et al. | | EP | 0 775 483 A1 | 5/1997 |
| 2002/0131947 A1 | 9/2002 | Nakanishi | | EP | 0 775 698 A1 | 5/1997 |
| 2002/0141958 A1 | 10/2002 | Maio et al. | | EP | 0 790 243 A1 | 8/1997 |
| 2002/0150602 A1 | 10/2002 | Livoreil et al. | | EP | 0 796 851 A1 | 9/1997 |
| 2002/0159964 A1 | 10/2002 | Nakanishi et al. | | EP | 0 797 976 A2 | 10/1997 |
| 2002/0168335 A1 | 11/2002 | Collin | | EP | 0 820 764 A1 | 1/1998 |
| 2002/0172696 A1 | 11/2002 | Kohli et al. | | EP | 0 847 752 A1 | 6/1998 |
| 2002/0189030 A1 | 12/2002 | Collin | | EP | 0 863 145 A2 | 9/1998 |
| 2002/0192168 A1 | 12/2002 | Blin | | EP | 0 877 063 B1 | 11/1998 |
| 2003/0012764 A1 | 1/2003 | Collin | | EP | 0 878 469 A1 | 11/1998 |
| 2003/0026772 A1 | 2/2003 | Jager-Lezer et al. | | EP | 0 879 592 A2 | 11/1998 |
| 2003/0044367 A1 | 3/2003 | Simon et al. | | EP | 0 887 073 A1 | 12/1998 |
| 2003/0086883 A1 | 5/2003 | Feng et al. | | EP | 0 893 119 B1 | 1/1999 |
| 2003/0129211 A9 | 7/2003 | Livoreil et al. | | EP | 0 923 928 A1 | 6/1999 |
| 2003/0147837 A1 | 8/2003 | Cavazzuti et al. | | EP | 0 925 780 A1 | 6/1999 |
| 2003/0161807 A1 | 8/2003 | Lemann | | EP | 0 928 608 A2 | 7/1999 |
| 2003/0161848 A1 | 8/2003 | Ferrari et al. | | EP | 0 930 058 B1 | 7/1999 |
| 2003/0185780 A1 | 10/2003 | Ferrari et al. | | EP | 0 930 060 A1 | 7/1999 |
| 2003/0198613 A1 | 10/2003 | Feng et al. | | EP | 0 933 376 A2 | 8/1999 |
| 2004/0013625 A1 | 1/2004 | Kanji | | | | |

| | | | | | | |
|---|---|---|---|---|---|---|
| EP | 943 340 | 9/1999 | | JP | 02/200612 | 8/1990 |
| EP | 0 958 804 A2 | 11/1999 | | JP | 02/207014 | 8/1990 |
| EP | 0 958 805 A2 | 11/1999 | | JP | 2216279 A | 8/1990 |
| EP | 0 958 811 A1 | 11/1999 | | JP | 3014683 A | 1/1991 |
| EP | 0 959 066 A2 | 11/1999 | | JP | 04346909 A | 12/1992 |
| EP | 0 959 091 A1 | 11/1999 | | JP | 7179795 A | 7/1995 |
| EP | 0 967 200 A1 | 12/1999 | | JP | 7267827 A | 10/1995 |
| EP | 0 976 390 A1 | 2/2000 | | JP | 8225316 A | 9/1996 |
| EP | 0 984 025 A2 | 3/2000 | | JP | 9/20631 | 1/1997 |
| EP | 1 002 514 A1 | 5/2000 | | JP | 09/255560 | 9/1997 |
| EP | 1 031 342 A1 | 8/2000 | | JP | 9295922 A | 11/1997 |
| EP | 1 044 676 A2 | 10/2000 | | JP | 10/007527 | 1/1998 |
| EP | 1 048 282 A1 | 11/2000 | | JP | 10/120903 | 5/1998 |
| EP | 1 053 742 A1 | 11/2000 | | JP | 10/212213 | 8/1998 |
| EP | 1 062 944 A1 | 12/2000 | | JP | 10259344 A | 9/1998 |
| EP | 1 062 959 A1 | 12/2000 | | JP | 11106216 A | 4/1999 |
| EP | 1 064 919 A1 | 1/2001 | | JP | 11/335228 | 12/1999 |
| EP | 1 064 920 A1 | 1/2001 | | JP | 11/335242 | 12/1999 |
| EP | 1 066 814 A1 | 1/2001 | | JP | 11/335254 | 12/1999 |
| EP | 1 068 854 A1 | 1/2001 | | JP | 2000038314 A | 2/2000 |
| EP | 1 068 855 A1 | 1/2001 | | JP | 2000038316 A | 2/2000 |
| EP | 1 068 856 A | 1/2001 | | JP | 2000038317 A | 2/2000 |
| EP | 1 086 945 A1 | 3/2001 | | JP | 2000038321 A | 2/2000 |
| EP | 1 090 627 B1 | 4/2001 | | JP | 2000086427 A | 3/2000 |
| EP | 1 095 959 A2 | 5/2001 | | JP | 2000086429 A | 3/2000 |
| EP | 1 114 636 A1 | 7/2001 | | JP | 2000086438 A | 3/2000 |
| EP | 1 213 011 A1 | 6/2002 | | WO | WO86/04916 | 8/1986 |
| EP | 1 213 316 A2 | 6/2002 | | WO | WO87/03783 | 7/1987 |
| FR | 1 529 329 | 5/1968 | | WO | WO91/12793 | 9/1991 |
| FR | 2 232 303 | 3/1975 | | WO | WO93/04665 | 3/1993 |
| FR | 2 315 991 | 1/1977 | | WO | WO93/21763 | 11/1993 |
| FR | 2 416 008 | 8/1979 | | WO | WO93/23008 | 11/1993 |
| FR | 2 674 126 | 9/1992 | | WO | WO94/18261 | 8/1994 |
| FR | 2 785 179 | 5/2000 | | WO | WO94/21233 | 9/1994 |
| FR | 2 796 270 | 1/2001 | | WO | WO95/15741 | 6/1995 |
| FR | 2 796 271 | 1/2001 | | WO | WO95/24887 | 9/1995 |
| FR | 2 796 272 | 1/2001 | | WO | WO95/33000 | 12/1995 |
| FR | 2 796 273 | 1/2001 | | WO | WO96/15761 | 5/1996 |
| FR | 2 796 276 | 1/2001 | | WO | WO96/40044 | 12/1996 |
| FR | 2 796 550 | 1/2001 | | WO | WO97/17057 | 5/1997 |
| FR | 2 802 806 | 6/2001 | | WO | WO97/36573 | 10/1997 |
| FR | 2 804 014 | 7/2001 | | WO | WO98/17243 | 4/1998 |
| FR | 2 804 017 | 7/2001 | | WO | WO98/17705 | 4/1998 |
| FR | 2 804 018 | 7/2001 | | WO | WO98/22078 | 5/1998 |
| FR | 2 810 562 | 12/2001 | | WO | WO98/25922 | 6/1998 |
| FR | 2 811 225 | 1/2002 | | WO | WO98/27162 | 6/1998 |
| FR | 2 811 552 A1 | 1/2002 | | WO | WO98/42298 | 10/1998 |
| FR | 2 816 506 | 5/2002 | | WO | WO98/47470 | 10/1998 |
| FR | 2 817 739 | 6/2002 | | WO | WO98/52534 | 11/1998 |
| FR | 2 817 740 | 6/2002 | | WO | WO98/58623 | 12/1998 |
| FR | 2 817 742 | 6/2002 | | WO | WO99/24002 | 5/1999 |
| FR | 2 817 743 | 6/2002 | | WO | WO 00/27350 | 5/2000 |
| FR | 2 819 399 | 7/2002 | | WO | WO 00/40216 | 7/2000 |
| FR | 2 819 400 | 7/2002 | | WO | WO 00/61080 | 10/2000 |
| FR | 2 819 402 | 7/2002 | | WO | WO 00/61081 | 10/2000 |
| GB | 1 117 129 | 6/1968 | | WO | WO 00/74519 | 12/2000 |
| GB | 1 194 901 | 6/1970 | | WO | WO 01/51020 | 7/2001 |
| GB | 1 194 902 | 6/1970 | | WO | WO 01/52799 | 7/2001 |
| GB | 1 220 069 | 1/1971 | | WO | WO 01/97758 A2 | 12/2001 |
| GB | 1 273 004 | 5/1972 | | WO | WO 01/97773 A1 | 12/2001 |
| GB | 1 444 204 | 7/1976 | | WO | WO 02/03932 A2 | 1/2002 |
| GB | 1 539 625 | 1/1979 | | WO | WO 02/03935 A2 | 1/2002 |
| GB | 2 014 852 | 9/1979 | | WO | WO 02/03950 A2 | 1/2002 |
| GB | 2 021 411 A | 12/1979 | | WO | WO 02/03951 A2 | 1/2002 |
| GB | 2 147 305 A | 5/1985 | | WO | WO 02/47605 A2 | 6/2002 |
| GB | 2 196 978 A | 5/1988 | | WO | WO 02/47606 A2 | 6/2002 |
| JP | 50/58242 | 5/1975 | | WO | WO 02/47608 A2 | 6/2002 |
| JP | 53043577 A | 4/1978 | | WO | WO 02/47619 A2 | 6/2002 |
| JP | 56123909 A | 9/1981 | | WO | WO 02/47620 | 6/2002 |
| JP | 56166276 A | 12/1981 | | WO | WO 02/47622 A2 | 6/2002 |
| JP | 61065809 A | 4/1986 | | WO | WO 02/47627 A1 | 6/2002 |
| JP | 62061911 | 3/1987 | | WO | WO 02/47629 A1 | 6/2002 |
| JP | 2127568 A | 5/1990 | | WO | WO 02/47630 A1 | 6/2002 |

| WO | WO 02/47658 | 6/2002 |
| WO | WO 02/49583 A1 | 6/2002 |
| WO | WO 02/49601 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |
| WO | WO 2005/013887 A2 | 2/2005 |

OTHER PUBLICATIONS

PCT Application No. PCT/US01/47499; Title: Cosmetic Compositions Containing Heteropolymers and Oil-Soluble Cationic Surfactants and Methods of Using Same Inventors: Carlos Pinzon and Paul Thau filed Dec. 12, 2001.
PCT Application No. PCT/FR01/03965; Title Cosmetic Composition Comprising Hetero Polymers and a Solid Substance and Method of Using Same Inventors: Roberto Cavazzuti et al. filed Dec. 12, 2001.
PCT Application No. PCT/US01/47454; Title: Compositions Containing Heteropolymers and Oil-Soluble Polymers and Methods of Using Same Inventors: Carlos Pinzon and Paul Thau filed Dec. 12, 2001.
PCT Application No. PCT/US01/47497; Title: Compositions Containing Heteropolymers and Oil-Soluble Esters and Methods of Using Same Inventors: Carlos Pinzon and Paul Thau filed Dec. 12, 2001.
PCT Application No. PCT/US01/47496; Title: Compositions Containing Heteropolymers and Methods of Using Same Inventors: Carlos Pinzon and Paul Thau filed Dec. 12, 2001.
PCT Application No. PCT/FR01/03962; Title: Wax-Free Cosmetic Composition Structured in Rigid Form With a Polymer Inventors: Véronique Ferrari et al. International Filing Date Dec. 12, 2001.
PCT Application No. PCT/FR01/03963; Title: Wax-Free Cosmetic Composition Structured in Rigid Form With a Polymer Inventor: Véronique Ferrari International Filing Date Dec. 12, 2001.
Co-Pending Application No. unassigned; Title: Cosmetic Compositions Containing at Least One Heteropolymer and at Least One Organogelator filed May 3, 2002.
Co-Pending U.S. Appl. No. 09/685,577; Title: Compositions in Rigid Form Structured With a Polymer Inventors: Véronique Ferrari and Pascal Simon filed Oct. 11, 2000.
Co-Pending U.S. Appl. No. 09/685,578; Title: Composition Containing a Liquid Fatty Phase Gelled With a Polyamide Containing Ester End Groups Inventors: Véronique Ferrari filed Jul. 17, 2000.
Co-Pending U.S. Appl. No. 09/685,578; Title: Composition Containing a Liquid Fatty Phase Gelled With a Polyamide Containing Ester End Groups Inventors: Véronique Ferrari filed Oct. 11, 2000.
PCT Application No. PCT/US00/33596; Title Cosmetic Composition Comprising Hetero Polymers and a Solid Substance and Method of Using Same Inventors Robert Cavazzuti et al. International Filing Date: Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau filed Dec. 12, 2000.
Co-Pending U.S. Appl. No. 09/733,897; Title: Compositions Containing Heteropolymers and Methods of Using Same Inventors: Carlos Pinzon and Paul Thau filed Dec. 12, 2000 Amendment filed Jan. 4, 2002 (adding claims 41-102).
PCT Application No. PCT/IB00/02000; Title: Compositions Comprising at Least One Heteropolymer and at Least One Inert Filler and Methods for Use Inventor: Carlos Pinzon and Paul Thau International Filing Date: Dec. 12, 2000.
PCT Application No. PCT/IB00/02006; Title: Cosmetic Compositions Containing at Least One Heteropolymer and at Least One Gelling Agent and Methods of Using the Same Inventors: Carlos Pinzon and Paul Thau International Filing Date: Dec. 12, 2000.
English language DERWENT abstract of EP 0 879 592 A2.
English language DERWENT abstract of EP 0 887 073 A1.
English language DERWENT abstract of JP 11106216.
English language DERWENT abstract of 0 959 066 A2.
English language DERWENT abstract of EP 0 930 058 B1.
English language DERWENT abstract of EP 0 930 060 A1.
English language DERWENT abstract of EP 0 958 811 A1.
English language DERWENT abstract of EP 0 959 091 A1.
English language DERWENT abstract of EP 0 976 390 A1.
English language DERWENT abstract of EP 0 984 025 A2.
English language DERWENT abstract of FR 2 785 179.
English language DERWENT abstract of EP 1 002 514.
English language DERWENT abstract of EP 1 031 342 A1.
English language DERWENT abstract of EP 1 048 282 A1.
English language DERWENT abstract of EP 1 053 742.
English language DERWENT abstract of EP 1 064 919.
English language DERWENT abstract of EP 1 064 920.
English language DERWENT abstract of EP 1 066 814.
English language DERWENT abstract of EP 1 068 854 A1.
English language DERWENT abstract of EP 1 068 855 A1.
English language DERWENT abstract of EP 1 086 945 A1.
English language DERWENT abstract of EP 1 090 627 B1.
English language DERWENT abstract of FR 2 802 806.
English language DERWENT abstract of EP 1 114 636 A1.
English language DERWENT abstract of WO 02/055031 A1.
English language DERWENT abstract of FR 2 819 402.
English language DERWENT abstract of WO 02/056845 A1.
Co-Pending U.S. Appl. No. 09/971,028, Title: Methods of Dispersing at Least One Coloring Agent Using at Least One Heteropolymer filed Oct. 5, 2001.
Co-Pending U.S. Appl. No. 10/198,931, Title: Composition Comprising at Least One Heteropolymer and Fibers, and Methods of Using the Same filed Jul. 22, 2002.
Co-Pending U.S. Appl. No. 09/899,909, issued as U.S. Patent No. 6,432,391 on Aug. 13, 2002, Title: Transparent Scented Solid Cosmetic Composition filed Jul. 9, 2001.
Co-Pending U.S. Appl. No. 09/937,314; Title: A Transfer-Free Composition Comprising at Least One Fatty Phase That is Structured With at Least One Polymer filed: Sep. 24, 2001.
Co-Pending U.S. Appl. No. 10/129,377; Title: Cosmetic Compositions Comprising a Polymer Blend filed Dec. 11, 2001.
Co-Pending U.S. Appl. No. 10/012,051; Title: Use of a Polymer for Obtaining an Express Make-Up of Keratin Materials filed Dec. 11, 2001.
Co-Pending U.S. Appl. No. 10/012,052; Title: Cosmetic Composition Comprising a Wax and a Polymer Inventors: Nathalie Collin filed Dec. 11, 2001.
Co-Pending U.S. Appl. No. 10/046,568; Title: Nail Polish Composition Comprising a Polymer filed Jan. 16, 2002.
French Search Report in FR 0016161, dated Sep. 6, 2001.
International Search Report in PCT/FR01/03940, dated Mar. 13, 2002.
French Search Report in FR 0016163, dated Aug. 1, 2001.
International Search Report in PCT/FR01/03945, dated May 31, 2002.
International Search Report in PCT/FR01/03939, dated Apr. 15, 2002.
French Search Report in FR 0016164, dated Sep. 6, 2001.
International Search Report in PCT/FR01/03937, dated Apr. 23, 2002.
French Search Report in FR 0016180, dated Oct. 16, 2001.
International Search Report in PCT/FR01/03938, dated Jun. 10, 2002.
International Search Report in PCT/IB01/02780, dated Apr. 10, 2002.
International Search Report in PCT/US00/33596, dated Aug. 8, 2001.
International Search Report in PCT/IB00/02000, dated Aug. 8, 2001.
International Search Report in PCT/IB01/02833, dated May 24, 2002.
International Search Report in PCT/IB00/02006, dated Aug. 8, 2001.

International Search Report in PCT/IB01/02840, dated Jun. 11, 2002.
International Search Report in PCT/IB01/02820, dated May 27, 2002.
International Search Report in PCT/IB00/02002, dated Sep. 4, 2001.
International Search Report in PCT/IB01/02786, dated Oct. 2, 2002.
French Search Report in FR 0100479, dated Sep. 17, 2001.
International Search Report in PCT/FR02/00129, dated Jun. 14, 2002.
French Search Report in FR 0100623, dated Oct. 9, 2001.
International Search Report in PCT/FR02/00144, dated Jun. 14, 2002.
French Search Report in FR 0100620, dated Nov. 6, 2001.
International Search Report in PCT/FR02/00194, dated May 12, 2002.
French Search Report in FR 0114529, dated Aug. 26, 2002.
French Search Report in FR 0114530, dated Aug. 26, 2002.
English language DERWENT abstract of DE 195 43 988.
English language DERWENT abstract of DE 199 51 010.
English language DERWENT abstract of DE 38 43 892.
English language DERWENT abstract of DE 42 34 886.
English language DERWENT abstract of EP 0 169 997 B1.
English language DERWENT abstract of EP 0 557 196 B1.
English language DERWENT abstract of EP 0 749 748.
English language DERWENT abstract of EP 0 925 780 A1.
English language DERWENT abstract of EP 1 048 282.
English language DERWENT abstract of FR 2 796 272.
English language DERWENT abstract of FR 2 796 273.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English Language Abstract of FR 2 804 014 from esp@cenet.
English Language Abstract of FR 2 817 742 from esp@cenet.
English language abstract of JP 02/207014 from Patent Abstracts of Japan.
Office Action in co-pending U.S. Appl. No. 10/312,083 filed Sep. 28, 2005.
Bangham, A.D. et al. Diffusion of Univalent Ions across the Lamellae of Swollen Phospholipids, Journal of Molecular Biology, pp. 238-252, vol. 13, Aug. to Oct. 1965.
Co-Pending U.S. Appl. No. 10/182,830; Title: Cosmetic Composition Comprising Hetero Polymers and a Solid Substance and Method of Using Same filed Aug. 2, 2002.
Co-Pending U.S. Appl. No. 10/203,018; Title: Composition Comprising at Least One Hetero Polymer and at Least One Inert Filler and Methods for Use filed Aug. 5, 2002.
Co-Pending U.S. Appl. No. 10/203,254; Title: Cosmetic Compositions Containing at Least One Heteropolymer and at Least One Gelling Agent and Methods of Using the Same filed Aug. 7, 2002.
Co-Pending U.S. Appl. No. 10/494,864; Title: Composition Containing an Amino Acid N-Acylated Ester and a Polyamide-Structured UV Filter filed Nov. 23, 2004.
Co-Pending U.S. Appl. No. 10/699,780, Title: Methods of Dispersing at Least One Coloring Agent Using at Least One Heteropolymer filed Nov. 4, 2003.
Co-Pending U.S. Appl. No. 10/918,579, Title: Compositions Containing Heteropolymers and Oilsoluble Esters and Methods of Using Same filed Aug. 16, 2004.
Co-Pending U.S. Appl. No. 10/990,475, Title: Use of a Polymer for Obtaining an Express Make-Up of Keratin Materials filed Nov. 18, 2004.
Co-Pending U.S. Appl. No. 10/993,430, Title: Cosmetic Composition Comprising a Polymer Blend filed Nov. 22, 2004.
Co-Pending U.S. Appl. No. 10/993,431, Title: A Transfer-Free Composition Structured in Rigid Form by a Polymer filed Nov. 22, 2004.

Co-Pending U.S. Appl. No. 11/019,382, Title: Cosmetic Composition Comprising Two Different Hetero Polymers and Method of Using Same filed Dec. 23, 2004.
Estee Lauder's Amended Answer and Counterclaims, dated Apr. 21, 2005, in the on-going litigation *L'Oreal S.A., et al., v. The Estee Lauder Companies Inc., et al.*, Civil Action No. 04-1660 (D.N.J.).
Estee Lauder's Response to Plaintiff's First Set of Interrogatories (Nos. 1-6), dated Sep. 27, 2004, in the on-going litigation *L'Oreal S.A., et al. v. The Estee Lauder Companies, Inc. et al.*, Civil Action No. 04-1660 (D.N.J.).
Estee Lauder's Response to Plaintiff's Third Set of Interrogatories (Nos. 8-13), dated Jun. 21, 2005, in the on-going litigation *L'Oreal S.A., et al. v. The Estee Lauder Companies Inc., et al.*, Civil Action No. 04-1660 (D.N.J.).
Harry's Cosmeticology 375-383 (J.B. Wilkinson & R.J. Moore eds., Chemical Pub. 7th ed. 1982).
International Search Report in PCT/US03/41618, dated Mar. 11, 2005.
International Search Report in PCT/US04/01071, dated Feb. 22, 2005.
McCutcheon's vol. 1: Emulsifiers & Detergents, North American Edition MC Publishing Co., Glen Rock NJ (1993), pp. 272-273.
Office Action in co-pending U.S. Appl. No. 09/618,066, filed Dec. 21, 2001.
Office Action in co-pending U.S. Appl. No. 09/618,066, dated Jul. 15, 2002.
Office Action in co-pending U.S. Appl. No. 09/618,066, dated Jul. 16, 2003.
Office Action in co-pending U.S. Appl. No. 09/618,066, dated Nov. 19, 2003.
Office Action in co-pending U.S. Appl. No. 09/685,577, dated Aug. 11, 2004.
Office Action in co-pending U.S. Appl. No. 09/685,577, dated Jul. 15, 2002.
Office Action in co-pending U.S. Appl. No. 09/685,577, dated Jul. 16, 2003.
Office Action in co-pending U.S. Appl. No. 09/685,577, dated Nov. 19, 2003.
Office Action in co-pending U.S. Appl. No. 09/685,578, dated Aug. 11, 2004.
Office Action in co-pending U.S. Appl. No. 09/685,578, dated Feb. 8, 2005.
Office Action in co-pending U.S. Appl. No. 09/685,578, dated May 7, 2003.
Office Action in co-pending U.S. Appl. No. 09/685,578, dated Nov. 19, 2003.
Office Action in co-pending U.S. Appl. No. 09/733,897, dated Apr. 15, 2002.
Office Action in co-pending U.S. Appl. No. 09/733,897, filed Apr. 23, 2003.
Office Action in co-pending U.S. Appl. No. 09/733,897, filed Aug. 29, 2002.
Office Action in co-pending U.S. Appl. No. 09/733,897, filed May 6, 2004.
Office Action in co-pending U.S. Appl. No. 09/733,898, filed Apr. 25, 2005.
Office Action in co-pending U.S. Appl. No. 09/733,898, filed Apr. 29, 2003.
Office Action in co-pending U.S. Appl. No. 09/733,898, filed Aug. 28, 2002.
Office Action in co-pending U.S. Appl. No. 09/733,898, filed Dec. 23, 2003.
Office Action in co-pending U.S. Appl. No. 09/733,899, filed Apr. 7, 2004.
Office Action in co-pending U.S. Appl. No. 09/733,899, filed Apr. 9, 2003.
Office Action in co-pending U.S. Appl. No. 09/733,899, filed May 3, 2005.
Office Action in co-pending U.S. Appl. No. 09/733,899, filed Sep. 22, 2004.
Office Action in co-pending U.S. Appl. No. 09/733,900, filed Apr. 7, 2004.

Office Action in co-pending U.S. Appl. No. 09/733,900, filed Dec. 1, 2004.
Office Action in co-pending U.S. Appl. No. 09/733,900, filed Jul. 16, 2003.
Office Action in co-pending U.S. Appl. No. 09/733,900, filed Jun. 2, 2005.
Office Action in co-pending U.S. Appl. No. 09/749,036, filed Apr. 29, 2005.
Office Action in co-pending U.S. Appl. No. 09/749,036, filed Aug. 13, 2003.
Office Action in co-pending U.S. Appl. No. 09/749,036, filed Jul. 16, 2002.
Office Action in co-pending U.S. Appl. No. 09/749,036, filed May 5, 2004.
Office Action in co-pending U.S. Appl. No. 09/899,909, filed Dec. 18, 2001.
Office Action in co-pending U.S. Appl. No. 09/937,314, filed May 19, 2004.
Office Action in co-pending U.S. Appl. No. 09/971,028, filed Aug. 11, 2003.
Office Action in co-pending U.S. Appl. No. 09/971,028, filed Mar. 26, 2003.
Office Action in co-pending U.S. Appl. No. 10/012,029, filed Nov. 20, 2002.
Office Action in co-pending U.S. Appl. No. 10/012,029, filed Sep. 8, 2003.
Office Action in co-pending U.S. Appl. No. 10/012,051, filed Jan. 14, 2003.
Office Action in co-pending U.S. Appl. No. 10/012,051, filed May 14, 2004.
Office Action in co-pending U.S. Appl. No. 10/012,051, filed Oct. 3, 2003.
Office Action in co-pending U.S. Appl. No. 10/012,052, filed Aug. 9, 2004.
Office Action in co-pending U.S. Appl. No. 10/012,052, filed Nov. 6, 2003.
Office Action in co-pending U.S. Appl. No. 10/012,052, filed Jun. 3, 2005.
Office Action in co-pending U.S. Appl. No. 10/046,568, filed Dec. 30, 2003.
Office Action in co-pending U.S. Appl. No. 10/046,568, filed Jun. 12, 2003.
Office Action in co-pending U.S. Appl. No. 10/046,568, filed Nov. 5, 2002.
Office Action in co-pending U.S. Appl. No. 10/046,568, filed Sep. 22, 2004.
Office Action in co-pending U.S. Appl. No. 10/047,987, filed Dec. 11, 2003.
Office Action in co-pending U.S. Appl. No. 10/047,987, filed Sep. 7, 2004.
Office Action in co-pending U.S. Appl. No. 10/182,830, filed Apr. 4, 2005.
Office Action in co-pending U.S. Appl. No. 10/182,830, filed Aug. 24, 2004.
Office Action in co-pending U.S. Appl. No. 10/198,931, filed Dec. 18, 2003.
Office Action in co-pending U.S. Appl. No. 10/198,931, filed Sep. 1, 2004.
Office Action in co-pending U.S. Appl. No. 10/203,018, filed May 19, 2004.
Office Action in co-pending U.S. Appl. No. 10/203,254, filed Apr. 22, 2005.
Office Action in co-pending U.S. Appl. No. 10/203,375, filed May 13, 2005.
Office Action in co-pending U.S. Appl. No. 10/312,083, filed Apr. 18, 2005.
Office Action in co-pending U.S. Appl. No. 10/312,083, filed Oct. 1, 2004.
Office Action in co-pending U.S. Appl. No. 10/413,217, filed Sep. 9, 2004.
Office Action in co-pending U.S. Appl. No. 10/699,780, filed Sep. 22, 2004.
Office Action in co-pending U.S. Appl. No. 10/699,780, filed Jun. 15, 2005.
Office Action in co-pending U.S. Appl. No. 10/746,612, filed Jun. 15, 2005.
Office Action in co-pending U.S. Appl. No. 10/746,612, filed Sep. 20, 2004.
Office Action in co-pending U.S. Appl. No. 10/787,440, filed Aug. 24, 2004.
Office Action in co-pending U.S. Appl. No. 10/787,441, filed Apr. 5, 2005.
Origins Full StoryTM Lush lash mascara product packaging, believed to have first been sold in 2003.
U.S. District Court for the District of New Jersey Civil Docket for *L'Oreal S.A. et al.* v. *Estee Lauder Companies, Inc., et al.*, Civ. No. 04-1660 (HAA) (filed Apr. 7, 2004) (retrieved Jan. 2, 2005).
Co-pending U.S. Appl. No. 11/212,811, Title: A Transfer-Free Mascara Composition Comprising at Least One Volatile Solvent and at Least One Polymer filed Aug. 29, 2005.
Co-pending U.S. Appl. No. 11/312,338, Title: Composition and Process for Coating Keratin Fibers filed Dec. 21, 2005.
Co-pending U.S. Appl. No. 11/351,309, Title: Cosmetic Composition Containing a Polymer and a Fluoro Oil filed Feb. 10, 2006.
Co-pending U.S. Appl. No. 11/406,371; Title: Cosmetic Composition Comprising Silica Particles, Reflecting Particles, and at Least One Polymer, Preparative Process, and Uses Thereof filed Apr. 19, 2006.
Estee Lauder's Answer and Counterclaims, dated May 27, 2004, in the on-going litigation *L'Oreal S.A., et al.,* v. *The Estee Lauder Companies Inc., et al.*, Civil Action No. 04-1660 (D.N.J.).
L'Oreal's Complaint for Patent Infringement, dated Apr. 7, 2004, in the on-going litigation *L'Oreal S.A., et al.,* v. *The Estee Lauder Companies Inc., et al.*, Civil Action No. 04-1660 (D.N.J.).
Office Action in co-pending U.S. Appl. No. 09/733,897, filed Feb. 8, 2006.
Office Action in co-pending U.S. Appl. No. 09/733,898, filed Jan. 11, 2006.
Office Action in co-pending U.S. Appl. No. 09/749,036, filed Nov. 23, 2005.
Office Action in co-pending U.S. Appl. No. 10/129,377, filed Jan. 13, 2006.
Office Action in co-pending U.S. Appl. No. 10/182,830, filed Nov. 25, 2005.
Office Action in co-pending U.S. Appl. No. 10/182,830, filed May 17, 2006.
Office Action in co-pending U.S. Appl. No. 10/203,254, filed Dec. 5, 2005.
Office Action in co-pending U.S. Appl. No. 10/312,083, filed Sep. 28, 2005.
Office Action in co-pending U.S. Appl. No. 10/312,083, filed Apr. 6, 2006.
Office Action in co-pending U.S. Appl. No. 10/746,612, filed Feb. 17, 2006.
Office Action in co-pending U.S. Appl. No. 10/990,475, filed May 1, 2006.
Office Action in co-pending U.S. Appl. No. 10/990,475, filed Nov. 2, 2005.
Office Action in co-pending U.S. Appl. No. 11/212,811, filed Nov. 17, 2005.
Richard J. Lewis, Sr., "Fatty Acid," Hawley's Condensed Chemical Dictionary 487 (13th ed., 1997).
Milan Jokić et al., *A Novel Type of Small Organic Gelators: Bis(Amino Acid) Oxalyl Amides*, 1995 J. Chem. Soc., Chem. Commun., 1723.
Kenji Hanabusa et al., *Prominent Gelation and Chiral Aggregation of Alkylamides Derived from trans-1,2-Diaminocyclohexane*, Angew. Chem. Int. Ed. Engl. 1996, 35, No. 17, 1949-1951.
Toshimi Shimizu et al., *Stereochemical Effect of Even-Odd Connecting Links to Supramolecular Assemblies Made of 1-Glucosamide Bolaamphiphiles*, J. Am Chem. Soc. 1997, 119, 2812-2818.
P. Terech, "Low-Molecular Weight Organogelators," in *Specialist Surfactants*, ch. 8, pp. 208-268 (I.D. Robb, ed., 1997).

Co-Pending U.S. Appl. No. 09/733,899; Title: Cosmetic Compositions Containing at Least One Heteropolymer and at Least One Film-Forming Silicone Resin and Methods of Using Inventors: Mohamed Kanji et al. filed Dec. 12, 2000.

Co-Pending U.S. Appl. No. 09/733,900; Title: Cosmetic Compositions Containing Heteropolymers and Oil-Soluble Cationic Surfactants and Methods of Using Same Inventors: Carlos Pinzon and Paul Thau filed Dec. 12, 2000.

Co-Pending U.S. Appl. No. 09/618,066; Title: Compositions in Rigid Form Structured With a Polymer Inventors: Véronique Ferrari and Pascal Simon filed Jul. 17, 2000.

International Search Report in PCT/US01/47454, dated Aug. 29, 2002.

International Search Report in PCT/US01/47499, dated Aug. 8, 2002.

Partial International Search Report in PCT/US01/47497, dated Aug. 30, 2002.

Co-Pending U.S. Appl. No. 09/618,032; Issued as U.S. Patent No. 6,402,408 on Jun. 11, 2002, Title: Composition Comprising a Liquid Fatty Phase Gelled With a Polyamide Containing Ester End Groups Inventor: Véronique Ferrari filed Jul. 17, 2000.

Co-Pending U.S. Appl. No. 10/012,029; Title: Cosmetic Compositions Comprising a Polymer Blend filed Dec. 11, 2001.

Co-Pending U.S. Appl. No. 10/413,217, Title: Methods of Dispersing at Least One Coloring Agent Using at Least One Heteropolymer filed Apr. 15, 2003.

Co-Pending U.S. Appl. No. 10/450,108, Title: Cosmetic Composition Comprising a Polymer and Fibres filed Jun. 11, 2003.

Co-Pending U.S. Appl. No. 10/459,636, Title: Cosmetic Emulsions Containing at Least One Hetero Polymer and at Least One Sunscreen and Methods of Using the Same filed Jun. 12, 2003.

Co-Pending U.S. Appl. No. 10/466,166, Title: Cosmetic Composition Comprising a Mixture of Polymers filed Jul. 14, 2003.

Co-Pending U.S. Appl. No. 10/618,315, Title: Cosmetic Compositions Comprising a Structuring Agent, Silicone Powder and Swelling filed Jul. 11, 2003.

Co-Pending U.S. Appl. No. 10/746,612, Title: Cosmetic Compositions Comprising a Structuring Agent, Silicone Powder and Swelling Agent filed Dec. 22, 2003.

Co-Pending U.S. Appl. No. 10/747,412, Title: Cosmetic Emulsions Containing at Least One Hetero Polymer and at Least One Sunscreen and Methods of Using the Same filed Dec. 22, 2003.

Co-Pending U.S. Appl. No. 10/787,440, Title: Compositions Comprising at Least One Hetero Polymer and at Least One Inert Filler and Methods for Use filed Feb. 27, 2004.

Co-Pending U.S. Appl. No. 10/787,441, Title: Cosmetic Compositions Comprising Hetero Polymers and a Solid Substance and Method of Using Same filed Feb. 27, 2004.

Handbook of Cosmetic Science and Tech. Elsevier Advanced Tech., 1st Edition (1994), p. 19.

International Search Report in PCT/FR01/03726, dated Apr. 9, 2002.

Kirk-Othmer, "Encyclopedia of Chemical Technology", Third Edition, vol. 22, John Wiley & Sons, 1983, pp. 332-342.

PCT Application No. PCT/US04/01071; Title: Long Wear Cosmetic Composition Inventor: Balanda ATIS International filing date: Jan. 16, 2004.

PCT Application No. PCT/US03/41618; Title: Cosmetic Compositions Comprising a Structuring Agent, Silicone Powder and Swelling Agent Inventor: Shao Xiang Lu, Terry Van Liew, Nathalie Geffroy-Hyland International filing date: Dec. 22, 2003.

Charles M. Hansen, "*The Three Dimensional Solubility Parameter—Key to Paint Component Affinities: I. Solvents, Plasticizers, Polymers, and Resins*," Journal of Paint Technology, vol. 39, No. 505, Feb. 1967, pp. 104-117.

Yasuda et al.,*Novel Low-molecular-weight Organic Gels: N,N', N''-Tristearyltrimesamide/Organic Solvent System*, Chemistry Letters, pp. 575-576, 1996, the month of publication is not available.

Bush Boake Allen, Inc., *Uniclear Formulations*, dated Oct. 13, 1998.

PCT Application No. PCT/IB01/02780; Title: Cosmetic Compositions Containing at Least One Heteropolymer and at Least One Organogelator International filing date: Dec. 12, 2001.

Co-Pending U.S. Appl. No. 10/047,987, Title: Cosmetic Composition Containing a Polymer and a Fluoro Oil filed Jan. 17, 2002.

Co-Pending U.S. Appl. No. 10/312,083, Title: Solid Emulsion Containing a Liquid Fatty Phase Structured With a Polymer filed Dec. 23, 2002.

Co-Pending U.S. Appl. No. 10/203,375, Title: Transparent or Translucent Colored Cosmetic Composition filed Aug. 9, 2002.

Co-Pending U.S. Appl. No. 10/203,374, Title: Method for Making a Coloured Make-Up Cosmetic Composition With Controlled Transmittance filed Aug. 9, 2002.

International Search Report in PCT/US01/47459, dated Feb. 6, 2003.

International Search Report in PCT/US01/47496, dated Feb. 26, 2003.

International Search Report in PCT/US01/47497, dated Dec. 2, 2002.

French Search Report in FR 9909176, dated Mar. 23, 2000.

French Search Report in FR 9916588, dated Oct. 16, 2000.

French Search Report in FR 0001004, dated Nov. 10, 2000.

French Search Report in FR 0000920, dated Nov. 10, 2000.

International Search Report in PCT/FR01/00229, dated Jan. 24, 2000.

French Search Report in FR 0008084, dated Mar. 28, 2001.

International Search Report in PCT/FR01/01958, dated Oct. 26, 2001.

French Search Report in FR 0008913, dated Mar. 28, 2001.

* cited by examiner

COMPOSITIONS COMPRISING HETEROPOLYMERS AND AT LEAST ONE OIL-SOLUBLE POLYMERS CHOSEN FROM ALKYL CELLULOSES AND ALKYLATED GUAR GUMS

The present invention relates to compositions and methods for care of, for treating, and for making-up at least one keratinous material, in particular at least one human keratinous material, such as skin, including the scalp, and the lips, and/or at least one keratinous fiber which includes hair, eyelashes, and eyebrows. More particularly, the compositions of the invention comprise at least one structuring polymer and at least one oil-soluble polymer chosen from alkyl celluloses and alkylated guar gums. The compositions may further comprise at least one fatty alcohol. This invention may be in the form of a stable composition such as, for example, make-up sticks, lipsticks, transparent sticks, and sunscreen sticks. The compositions may also, for example, result in a molded composition.

The use of high molecular weight polyamides to produce clear stick compositions dates back to the mid 1960's. These systems contained a combination of polyamide polymer, castor oil, esters, amides, and colorants as described in, for example, U.S. Pat. Nos. 3,086,914 and 3,148,125. However, there were significant drawbacks associated with such compositions. For example, the sticks were tacky and difficult to apply to the lips. During storage, particularly at slightly elevated temperatures, the stick surface developed distinct oil droplets (syneresis) which were not reabsorbed after the stick cooled to normal room temperature.

There have been many attempts to resolve the aforementioned technical problems with only partial success. The introduction of new specialty cosmetic esters has made it possible to reduce product tackiness and thereby improve application characteristics. However, these modifications did not diminish the tendency of these formulations to have stability problems such as developing distinct and unattractive oil syneresis. In some instances, these modified formulations also displayed poor temperature stability at 50° C.

The inventors have found that the use of specific structuring polymers and oil-soluble polymers may result in a stable composition. In one embodiment, the compositions of the invention also may provide good gelling efficiency and/or maintain desirable cosmetic application properties.

In one embodiment, the invention provides a composition comprising at least one structuring polymer comprising a polymer skeleton which comprises at least one hydrocarbon-based repeating unit comprising at least one hetero atom. The composition further comprises at least one oil-soluble polymer chosen from alkyl celluloses and alkylated guar gums. In a further embodiment, the at least one structuring polymer and the at least one oil-soluble polymers are present in a combined amount effective to stabilize the composition. As used herein, the expression "at least one" means one or more and thus includes individual components as well as mixtures and combinations thereof.

The invention also provides a method for providing stability to a composition comprising including in the composition at least one structuring polymer comprising a polymer skeleton which comprises at least one hydrocarbon-based repeating unit comprising at least one hetero atom. The composition further comprises at least one oil-soluble polymer chosen from alkyl celluloses and alkylated guar gums.

The invention also provides for a cosmetic process for caring for, making up, and/or treating a keratinous material comprising applying to at least one keratinous material a cosmetic composition comprising at least one structuring polymer comprising a polymer skeleton which comprises at least one hydrocarbon-based repeating unit comprising at least one hetero atom. The composition further comprises at least one oil-soluble polymer chosen from alkyl celluloses and alkylated guar gums. As used herein, "keratinous material" is meant to comprise hair, lips, skin, scalp and superficial body growths such as eyelashes, eyebrows and nails.

It is to be understood that both the foregoing general description and the following detailed description are exemplary and explanatory only and are not restrictive of the invention as claimed.

One subject of the invention is cosmetic and/or dermatological compositions which are useful for the care, make-up and/or treatment of at least one keratinous material which may be of suitable hardness to allow preparation of these compositions in the form of a stick or other structured form which may be stable.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as bending or leaning if the composition is in stick form, phase separation, melting, or syneresis. As used herein, syneresis is the appearance of droplets on the surface of a composition that are visible to the naked eye. Syneresis or oil release from a composition, such as a stick, that is only apparent as a thin, attractive, and glossy, surface coating is not considered a composition that has failed the stability test. The stability is further tested by repeating the 8 week test at 4° C., 37° C., 45° C., and 50° C., and under freeze-thaw conditions. A composition is considered to lack stability if an abnormality that impedes functioning of the composition is observed in any of these tests. The skilled artisan will readily recognize an abnormality that impedes functioning of a composition based on the intended application.

The invention applies not only to make-up products for at least one keratinous material such as lip compositions, lip pencils, foundations including foundations which may be cast in the form of a stick or a dish, concealer products, temporary tattoo products, eyeliners, and mascara bars, but also to body hygiene products such as deodorant sticks, and to care products and products for treating at least one keratinous material such as sunscreen and after-sun products which may be in stick form and also nail products. It is to be noted that a deodorant product is a body hygiene product and does not relate to care, make-up, or treatment of keratin materials, including keratinous fibers, skin, or lips.

The present invention may be in the form of a mascara product, an eyeliner product, a foundation product, a lipstick product, a lip balm, a blush for cheeks or eyelids, a deodorant product, a fragrance product, a make-up product for the body, a make-up-removing product, an eyeshadow product, a face powder product, a night or day care product for the face, a concealer product, a hair conditioning product, a sun screen, a colorant for the skin or hair, or a skin care formula such as, for example, anti-pimple, or shaving cut formulas. According to one embodiment of the invention, the composition is in the form of a substantially clear or substantially transparent composition such as, for example, a clear lipstick, clear sunscreen composition, or clear foundation, in particular for concealing skin imperfections.

For example, the composition of the present invention may be in a form chosen from a paste, a solid, a gel, and a cream. It may be an emulsion, i.e., an oil-in-water or water-in-oil emulsion, a multiple emulsion, e.g., an oil-in-water-in-oil emulsion or water-in-oil-in-water emulsion, or a solid, rigid, or supple gel, including anhydrous gels. In one embodiment, the composition of the invention comprises an external fatty phase or a continuous fatty phase, which fatty phase can be anhydrous. In another embodiment, the composition of the invention is transparent or clear. The composition can also be in a form chosen from a translucent anhydrous gel and a transparent anhydrous gel. The composition can also be a molded composition or cast as a stick or a dish. The composition in one embodiment is a solid or rigid product, such as a molded stick or a poured stick.

Structuring Polymer

In one embodiment, the at least one structuring polymer in the composition of the invention is a solid that is not deformable at room temperature (25° C.) and atmospheric pressure (760 mmHg). In a further embodiment, the at least one structuring polymer is capable of structuring the composition without opacifying it. As defined above, the at least one structuring polymer of the present invention comprises a polymer skeleton comprising at least one hydrocarbon-based repeating unit comprising at least one hetero atom. In one embodiment, the at least one structuring polymer further comprises at least one terminal fatty chain chosen from alkyl and alkenyl chains, such as of at least 4 atoms, and further such as comprising 8 to 120 carbon atoms, bonded to the polymer skeleton via at least one linking group. The terminal fatty chain may, for example, be functionalized. The at least one structuring polymer may also further comprise at least one pendant fatty chain chosen from alkyl and alkenyl chains, such as of at least 4 atoms, and further such as comprising 8 to 120 carbon atoms, bonded to any carbon or hetero atom of the polymer skeleton via at least one linking group. The pendant fatty chain may, for example, be functionalized. The at least one structuring polymer may comprise both at least one pendant fatty chain and at least one terminal fatty chain as defined above, and one or both types of chains can be functionalized.

In one embodiment, the structuring polymer comprises at least two hydrocarbon-based repeating units. As a further example, the structuring polymer comprises at least three hydrocarbon-based repeating units and as an even further example, the at least three repeating units are identical.

As used herein, "functionalized" means comprising at least one functional group. Non-limiting examples of functional groups include hydroxyl groups, ether groups, oxyalkylene groups, polyoxyalkylene groups, carboxylic acid groups, amine groups, amide groups, halogen containing groups, including fluoro and perfluoro groups, halogen atoms, ester groups, siloxane groups and polysiloxane groups.

For purposes of the invention, the expression "functionalized chain" means, for example, an alkyl chain comprising at least one functional (reactive) group chosen, for example, from those recited above. For example, in one embodiment, the hydrogen atoms of at least one alkyl chain may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units, such as, for example, a compound containing at least 3 repeating units, which may be identical.

As used herein, the expression "hydrocarbon-based repeating unit" includes a repeating unit comprising from 2 to 80 carbon atoms, such as, for example, from 2 to 60 carbon atoms. The at least one hydrocarbon-based repeating unit may also comprise oxygen atoms. The hydrocarbon-based repeating unit may be chosen from saturated and unsaturated hydrocarbon-based repeating units which in turn may be chosen from linear hydrocarbon-based repeating units, branched hydrocarbon-based repeating units and cyclic hydrocarbon-based repeating units. The at least one hydrocarbon-based repeating unit may comprise, for example, at least one hetero atom that is part of the polymer skeleton, i.e., not pendant. The at least one hetero atom may be chosen, for example, from nitrogen, sulphur, and phosphorus. For example, the at least one hetero atom may be a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

The at least one repeating unit comprising at least one hetero atom may be chosen, for example, from amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the hetero atoms of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the compositions of the invention comprise at least one structuring polymer with nitrogen atoms, such as amide, urea, or carbamate units, such as amide units, and at least one polar oil.

In one embodiment, in the at least one structuring polymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one structuring polymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units containing a hetero atom, and in high proportion, which corresponds to the presence of several hetero atoms, the greater the affinity of the at least one structuring polymer to polar oils. Conversely, the more non-polar, or even apolar, and lesser in proportion the hydrocarbon-based repeating units containing a hetero atom, the greater the affinity of the polymer for apolar oils.

In another embodiment, the invention is drawn to a structured composition containing at least one liquid fatty phase structured with at least one structuring polymer, wherein said at least one structuring polymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains at least one oil-soluble polymer chosen from alkyl celluloses and alkylated guar gums. The at least one liquid fatty phase, the at least one structuring polyamide and the at least one oil-soluble polymer chosen from alkyl celluloses and alkylated guar gums together form a physiologically acceptable medium.

When the structuring polymer has amide repeating units, the pendant fatty chains may be linked to at least one of the nitrogen atoms in the amide repeating units.

The structuring polymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

As discussed, the at least one structuring polymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via said at least one linking group. In one embodiment, the at least one linking group is chosen from single bonds and urea, urethane, thiourea, thiourethane, thioether, thioester, ester, ether and amine groups. For example, the linking group can be chosen from ureas, esters, and amines. As a further example, the linking group can be chosen from esters and amines. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polyamide polymers of formula (I):

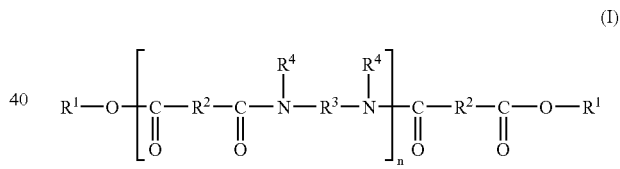

in which:

n is an integer which represents the number of amide units such that the number of ester groups present in said at least one polyamide polymer ranges from 10% to 50% of the total number of all said ester groups and all said amide groups comprised in the at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In the polymer of formula (I), the terminal fatty chains that are optionally functionalized for the purposes of the invention are terminal chains linked to the last hetero atom, in this case nitrogen, of the polyamide skeleton.

In one embodiment, the ester groups of formula (I), which form part of the terminal and/or pendant fatty chains for the purposes of the invention, are present in an amount ranging from 15% to 40% of the total number of ester and amide groups, such as from 20% to 35%.

In formula (I), in one embodiment, n may be an integer ranging from 1 to 5, for example an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ hydrocarbon-based, e.g., alkylene groups. At least 50% of all $R^2$, for example at least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{18}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of an at least one polyamide polymer which may be used in the composition according to the present invention include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of an at least one polyamide polymer which may be used in the compositions according to the present invention include polyamide polymers resulting from the condensation of at least one aliphatic dicarboxylic acid and at least one diamine, the carbonyl and amine groups being condensed via an amide bond. In one embodiment, these polymers contain more than two carbonyl groups and more than two amine groups. Examples of these polyamide polymers are those sold under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6000 to 9000. For further information regarding these polyamides, reference may be made to U.S. Pat. Nos. 3,645,705 and 3,148,125, the disclosures of which are hereby incorporated by reference. In one embodiment, Versamid 930 or 744 may be used.

Other examples of polyamides include those sold by the company Arizona Chemical under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

The at least one structuring polymer in the compositions of the invention may have a softening point greater than 50° C., such as from 65° C. to 190° C., and further such as from 70° C. to 130° C., and even further such as from 80° C. to 105° C. This softening point may be lower than that of structuring polymers used in the art which may facilitate the use of the at least one structuring polymer of the present invention and may limit the degradation of the liquid fatty phase. These polymers may be non waxy polymers.

In one embodiment, the at least one structuring polymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one structuring polymer, unlike polymers not containing a fatty chain.

The at least one structuring polymer may be present in the composition in an amount ranging, for example, from 0.5% to 80% by weight relative to the total weight of the composition, such as for example 2% to 60%, and further, for example, from 5 to 40%. In a further embodiment the at least one structuring polymer may be present in the composition in an amount ranging, for example, from 5% to 25% by weight relative to the total weight of the composition.

When the at least one structuring polymer of the present invention comprises a urea urethane having the following formula:

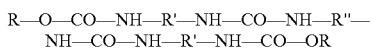

then R represents $C_nH_{2n+1}$, wherein n represents an integer having a value greater than 22, for example from 23 to 120, and further, for example from 23 to 68, or $C_mH_{2m+1}(OC_pH_{2p})_r$—, wherein m represents an integer having a value of greater than 18, for example from 19 to 120, and further, for example, from 23 to 68, p represents an integer having a value of from 2 to 4, and r represents an integer having a value of from 1 to 10, R' represents:

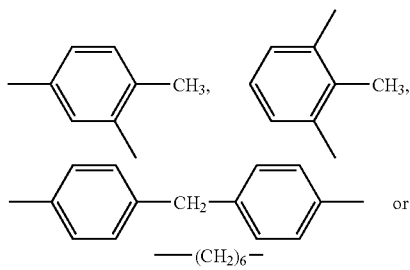

and R" represents:

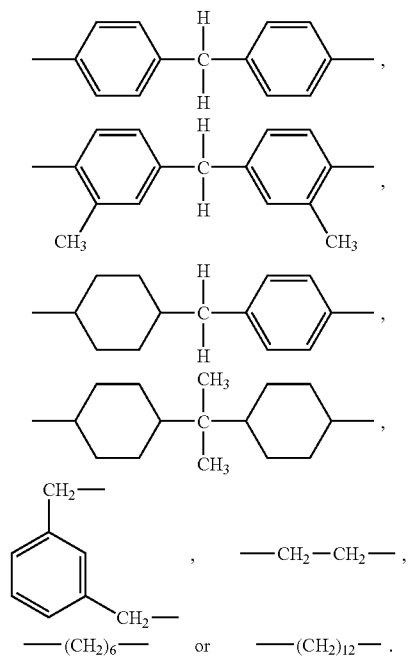

In another embodiment of the invention, the present invention is drawn to a structured composition comprising at least one liquid fatty phase structured with at least one structuring polymer comprising a polymer skeleton comprising at least one hydrocarbon-based repeating unit comprising at least one hetero atom, wherein the at least one structuring polymer further comprises at least one terminal fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to the polymer skeleton via at least one linking group chosen from amides, ureas, and esters, wherein when said at least one linking group is chosen from esters, said at least one terminal fatty chain is chosen from branched alkyl groups. The at least one structuring polymer may also comprise at least one pendant fatty chain, optionally functionalized, chosen from alkyl and alkenyl chains, such as alkyl and alkenyl chains having at least four carbon atoms, and further such as alkyl and alkenyl chains comprising from 8 to 120 carbon atoms, bonded to any carbon or hetero atom of the polymer skeleton via at least one linking group chosen from amides, ureas, and esters, wherein when said at least one linking group is chosen from esters, said at least one terminal fatty chain is chosen from branched alkyl groups. The at least one structuring polymer may comprise both at least one pendant fatty chain and at least one terminal fatty chain as defined above in this paragraph.

Further, an embodiment of the invention relates to a skin, lip, or keratinous fiber care, treatment, or make-up composition comprising a structured composition containing at least one liquid fatty phase structured with at least one structuring polymer comprising a polymer skeleton comprising at least one hydrocarbon-based repeating unit comprising at least one hetero atom and at least one oil-soluble polymer chosen from alkyl celluloses and alkylated guar gums.

Additionally, an embodiment of the invention relates to a skin, lip, or keratinous fiber care or make-up composition comprising a structured composition containing at least one liquid fatty phase structured with at least one structuring polymer comprising a polymer skeleton comprising at least one hydrocarbon-based repeating unit comprising at least one hetero atom, at least one oil-soluble polymer chosen from alkyl celluloses and alkylated guar gums, and at least one coloring agent.

Additionally, an embodiment of the invention relates to a method of making up skin or lips or making up keratinous fibers or caring for skin or lips or caring for keratinous fibers comprising applying to said skin, lips, or keratinous fibers a structured composition containing at least one liquid fatty phase structured with at least one structuring polymer comprising a polymer skeleton comprising at least one hydrocarbon-based repeating unit comprising at least one hetero atom and at least one oil-soluble polymer chosen from alkyl celluloses and alkylated guar gums.

The at least one structuring polymer has an affinity with the fatty phase and in particular with a chemical portion of one of the oils forming the liquid fatty phase of the composition so that physical links with the oils, such as hydrogen bonds are formed.

Liquid Fatty Phase

The at least one liquid fatty phase, in one embodiment, may comprise at least one oil. The at least one oil, for example, may be chosen from polar oils and apolar oils including hydrocarbon-based liquid oils and oily liquids at room temperature. In one embodiment, the compositions of the invention comprise at least one structuring polymer and at least one polar oil. The polar oils of the invention, for example, may be added to the apolar oils, the apolar oils acting in particular as co-solvent for the polar oils.

According to the invention, the structuring of the at least one liquid fatty phase may be obtained with the aid of at least one structuring polymer, such as the polymer of formula (I).

In general, the polymers of formula (I) may be in the form of mixtures of polymers, these mixtures also possibly containing a synthetic product corresponding to a compound of formula (I) in which n is 0, i.e., a diester.

The liquid fatty phase of the composition may contain more than 30%, for example, more than 40%, of liquid oil(s) having a chemical nature close to the chemical nature of the skeleton (hydrocarbon or silicone based) of the structuring polymer, and for example from 50% to 100%. In one embodiment, the liquid fatty phase structured with a polyamide-type skeleton, or polyurea, or polyurethane, or polyurea-urethane-type skeleton contains a high quantity, i.e., greater than 30%, for example greater than 40% relative to the total weight of the liquid fatty phase, or from 50% to 100%, of at least one apolar, such as hydrocarbon-based, oil. For the purposes of the invention, the expression "hydrocarbon-based oil" means an oil comprising carbon and hydrogen atoms, optionally with at least one group chosen from hydroxyl, ester, carboxyl and ether groups.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

For a liquid fatty phase structured with an apolar polymer of the hydrocarbon-based type, this fatty phase may contain more than 30%, for example more than 40% by weight, and, as a further example, from 50% to 100% by weight, of at least one liquid apolar, such as hydrocarbon-based, oil, relative to the total weight of the liquid fatty phase.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear and branched, and saturated and unsaturated chains; these oils can be chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula $R_5COOR_6$ in which $R_5$ is chosen from linear and branched fatty acid residues containing from 1 to 40 carbon atoms and $R_6$ is chosen from, for example, a hydrocarbon-based chain containing from 1 to 40 carbon atoms, on condition that $R_5+R_6 \geq 10$, such as, for example, purcellin oil (cetostearyl octanoate), isononyl isononanoate, $C_{12}$-$C_{15}$ alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

$C_8$ to $C_{26}$ fatty alcohols such as oleyl alcohol; and $C_8$ to $C_{26}$ fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; and mixtures thereof. The structured oils, for example those structured with polyamides such as those of formula (I) or with polyurethanes, polyureas, polyurea-urethanes, in accordance with the invention, may be, in one embodiment, apolar oils, such as an oil or a mixture of hydrocarbon oils chosen from those of mineral and synthetic origin, chosen from hydrocarbons such as alkanes such as Parleam® oil, isoparaffins including isododecane, and squalane, and mixtures thereof. These oils may, in one embodiment, be combined with at least one phenylsilicone oil.

The liquid fatty phase, in one embodiment, contains at least one non-volatile oil chosen from, for example, hydrocarbon-based oils of mineral, plant and synthetic origin, synthetic esters or ethers, silicone oils and mixtures thereof.

In practice, the total liquid fatty phase can be, for example, present in an amount ranging from 5% to 99% by weight relative to the total weight of the composition, for example from 10% to 80%, and, as a further example, from 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg and, for example, greater than 0.3 mmHg. The expression "non-volatile oil" means an oil which remains on the skin or the lips at room temperature and atmospheric pressure for at least several hours, such as those having a vapor pressure of less than $10^{-2}$ mmHg.

According to the invention, these volatile solvents may facilitate the staying power or long wearing properties of the composition on the skin, the lips or superficial body growths, such as keratinous fibers. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, is present in an amount ranging up to 95.5% relative to the total weight of the composition, such as from 2% to 75%, and, as a further example, from 10% to 45%. This amount will be adapted by a person skilled in the art according to the desired staying power or long wearing properties.

The at least one liquid fatty phase of the compositions of the invention may further comprises a dispersion of lipid vesicles. The compositions of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally containing dispersed lipid vesicles or oil droplets, or a fatty phase optionally containing dispersed lipid vesicles or water droplets. In one embodiment, the composition has a continuous oily phase or fatty phase and is more specifically an anhydrous composition, for example, a stick or dish form. An anhydrous composition is one that has less than 10% water by weight, such as, for example, less than 5% by weight.

Oil-Soluble Polymer

The compositions of the invention may further comprise at least one oil-soluble polymer chosen from alkylated guar gums and alkyl celluloses. Alkylated guar gums include, for example, ethyl guars and $C_{1-5}$ alkyl galactomannans, such as N-HANCE AG-50 and N-HANCE AG-200 from Aqualon. An alkyl cellulose, may be chosen from, for example, ethylcellulose (such as ETHOCEL, from Dow Chemical). In one embodiment, the at least one oil-soluble polymer may be present in the composition in an amount ranging from 0.05% to 10.0% by weight relative to the total weight of the composition, such as, for example 0.1% to 5% and 0.1% to 3%. These ingredients can further stabilize, for example, a clear sunscreen complex composition against syneresis.

In one embodiment, a composition according to the invention may be stabilized by the inclusion of at least one oil-soluble polymer chosen from alkyl celluloses. In a further embodiment, at least one alky galactomannan, such as N-HANCE AG-50, may be used to stabilize a stick composition against stick syneresis, particularly at elevated temperatures such as, for example, 45° C.

The concentrations of the at least one structuring polymer and of the at least one oil-soluble polymer chosen from alkyl celluloses and alkylated guar gums may be chosen according to the desired hardness and desired stability of the compositions and according to the specific application envisaged. The respective concentrations of the at least one polyamide polymer and of the at least one oil-soluble polymer chosen from alkyl celluloses and alkylated guar gums can be such that a disintegrable solid which does not flow under its own weight is obtained.

Depending on the intended application, such as a stick, hardness of the composition may also be considered. The hardness of a composition may, for example, be expressed in grams (g). The composition of the present invention may, for example, have a hardness ranging from 20 g to 2000 g, such as from 20 g to 900 g, and further such as from 20 g to 600 g. This hardness is measured in one of two ways. A first test for hardness is according to a method of penetrating a probe into said composition and in particular using a texture analyzer (for example TA-XT2 from Rhéo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 g.

The second test for hardness is the "cheese wire" method, which involves cutting an 8.1 mm tube of composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 g to 300 g, such as from 30 g to 250 g, and further such as from 30 g to 200 g.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

According to the present invention, the compositions in stick form may also possess the properties of deformable, flexible elastic solids and may also have noteworthy elastic softness upon application to a keratinous material. The compositions in stick form of the prior art do not have this elasticity and flexibility.

Fatty Alcohol

The compositions of the invention may further comprise at least one fatty alcohol. The at least one fatty alcohol may be chosen from, for example, $C_8$ to $C_{26}$, such as from, $C_{12}$ to $C_{22}$ fatty alcohols. In one embodiment, the at least one fatty alcohol is chosen from myristyl, cetyl, stearyl, and behenyl alcohol. The fatty alcohols may, for example, be present in the composition in an amount ranging from 0.1% to 15.0% by weight, relative to the total weight of the composition, such as, for example, 0.5% to 10% and 0.5% to 8.0%. In a further embodiment, the skilled artisan may be able to cure a stability defect by the addition of at least one fatty alcohol to the composition. For example, the addition of at least one fatty alcohol may improve stick structure, minimize syneresis, and generally improve application properties without interfering with stick transparency, as compared to a composition that does not contain the at least one fatty alcohol.

Oil-Soluble Ester

The compositions of the invention may also comprise at least one oil-soluble ester comprising at least one free hydroxy group. Any oil-soluble ester comprising at least one free hydroxy group may be within the practice of the invention with the proviso that said at least one oil-soluble ester is not castor oil.

The at least one oil-soluble ester comprising at least one free hydroxy group may be chosen from, for example, propylene glycol ricinoleate, isopropyl hydroxystearate, triisocetyl citrate, diisostearyl malate, octyl hydroxystearate, triisoarachidyl citrate, cetyl lactate, dioctyl malate, octyldodecyl hydroxystearate, di-isostearyl malate, and di-isostearyl lactate.

In one embodiment, the at least one oil-soluble ester comprising at least one free hydroxy group, such as diisostearyl malate and triisocetyl citrate may add stability. For example, the use of these esters may minimize oil droplet formulation at room temperature and elevated temperature storage. The introduction of at least one hydroxy bearing ester, in addition, may dramatically improve the overall softening point of the finished clear anhydrous stick.

In a further embodiment, certain at least one oil-soluble esters comprising at least one free hydroxy group may provide the firmest and clearest compositions and sticks and may also improve the gelling efficiency in relation to a composition comprising structuring polymers alone. For example, a composition comprising 16-20% structuring polymer with the at least one oil-soluble ester comprising at least one free hydroxy group chosen from isopropyl hydroxystearate had excellent clarity and structure.

Depending on the at least one structuring polymer and its concentration and the at least one oil-soluble ester comprising at least one free hydroxy group and its concentration, some compositions may develop syneresis after aging for one day at 25° C., which may be disadvantageous in certain embodiments. The skilled artisan may be able to cure this defect by varying the at least one structuring polymer and/or the at least one oil-soluble ester comprising at least one free hydroxy group. The skilled artisan may also be able to cure this defect by varying the concentration of at least one of these ingredients.

In one embodiment, the at least one oil-soluble ester comprising at least one free hydroxy group may be present in the composition in an amount ranging from 10% to 84% by weight relative to the total weight of the composition, such as, for example 20% to 70%.

Oil-Soluble Cationic Surfactant

As described above, the compositions of the invention may further comprise at least one oil-soluble cationic surfactant. In one embodiment, the at least one oil-soluble cationic surfactant may be chosen from lauryl methyl gluceth-10-hydroxypropyl dimmonium chloride, which may impart cosmetic elegance to a composition. The at least one oil-soluble cationic surfactant may also, for example, be chosen from quaternary ammonium compounds including salts of quaternary ammonium compounds and fatty amines including salts of fatty amines.

In one embodiment, the at least one oil-soluble cationic surfactant is chosen from water-insoluble surfactants of the formula

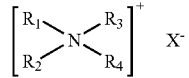

wherein $R_1$-$R_4$ is independently chosen from an aliphatic group of from 1 to 22 carbon atoms, $C_1$-$C_3$ alkyl, hydroxyalkyl, polyalkoxy, aromatic, aryl, and alkylaryl groups having from 12 to 22 carbon atoms; X is chosen from halogen, acetate, phosphate, nitrate, and alkylsulfate radicals. The aliphatic groups may, for example, contain in addition to carbon and hydrogen atoms, ether linkages, and other groups such as amino groups.

The at least one oil-soluble cationic surfactant may also, for example, be chosen from quaternary ammonium salts of the formula

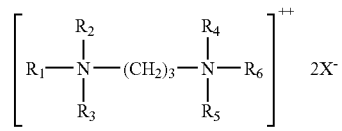

wherein $R_1$ is an aliphatic group having from 16 to 22 carbon atoms; $R_2$, $R_3$, $R_4$, $R_5$, and $R_6$ are independently chosen from hydrogen and alkyl having from 1 to 4 carbon atoms, and X is chosen from halogen, acetate, phosphate, nitrate, and alkyl sulfate radicals. The at least one oil-soluble cationic surfactant may, for example, be tallow propane diammonium dichloride.

Non-limiting examples of the at least one oil-soluble cationic surfactant include the quaternary ammonium salts: dialkyldimethyl-ammonium chlorides, wherein the alkyl groups have from 12 to 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms); ditallowdimethyl ammonium chloride; ditallowdimethyl ammonium methyl sulfate; dihexadecyl dimethyl ammonium chloride; di(hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium acetate; dihexadecyl dimethyl ammonium chloride, dihexadecyl dimethyl ammonium acetate; ditallow dipropyl ammonium phosphate; ditallow dimethyl ammonium nitrate; di(coconutalkyl) dimethyl ammonium chloride; dicetyl dimethyl ammonium chloride; stearyl dimethyl benzyl ammonium chloride; behenyl trimethyl ammonium chloride; Di-(hydrogenated tallow) dimethyl ammonium chloride.

Non-limiting examples of the at least one oil-soluble cationic surfactant also include salts of primary, secondary, and tertiary fatty amines. In one embodiment, salts of amines may comprise alkyl groups having from 12 to 22 carbon atoms, and may be substituted and unsubstituted. Amines may be chosen from, for example, stearamido propyl dimethyl amine, diethyl amino ethyl stearamide, dimethyl stearamine, dimethyl soyamine, soyamine, tridecyl amine, ethyl stearylamine, ethoxylated (2 moles E.O.) stearylamine, dihydroxyethyl stearylamine, and arachidyl-behenylamine. Amine salts may be chosen from, for example, halogens, actetates, phosphates, nitrates, citrates, lactates, and alkyl sulfates. In one embodiment, the amine salts are chose from stearylamine hydrochloride, soyamine chloride, stearylamine formate, N-tallowpropane diaminedichloride, and stearamidopropyl dimethylamine citrate. The at least one oil-soluble cationic surfactant may also be chosen from cationic amine surfactants disclosed in U.S. Pat. No. 4,275,055, the disclosure of which is hereby incorporated by reference.

In another embodiment, the at least one oil-soluble cationic surfactant may be chosen from quaternary imidazolinium compounds including quaternary imidazolinium salts. Quaternary imidazolinium compounds include, for example, imidazolinium compounds containing $C_{12}$-$C_{22}$ alkyl groups such as 1-methyl-1-[(stearoylamide)ethyl]-2-heptadecyl-4,5-dihydroimidazolinium chloride, 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate. The at least one oil-soluble cationic surfactant may also be chosen from conditioning agents that are disclosed in U.S. Pat. No. 4,387,090, to Bolich, issued Jun. 7, 1983, which is incorporated by reference herein.

The at least one oil-soluble cationic surfactant may be present in the composition, for example, in an amount ranging from 0.1% to 10% by weight relative to the weight of the composition, such as, for example, 0.1% to 5.0% and 0.5% to 2.0%. As used herein cosmetic elegance refers to substantially low tackiness, ease of application, or elegant feel.

Wax

According to another embodiment, the compositions of the invention may further comprise at least one wax. At least one wax, for example, may be used to form a non-transparent composition. As used herein, a "wax" may be any lipophilic fatty compound which is soluble in the liquid fatty phase, unlike most fillers or pigments. The at least one wax, for example, may have a melting point greater than about 45°, such as, for example greater than about 55° C. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, jojoba esters, waxes of synthetic origin, such as polyethylene waxes derived from polymerization of ethylene, waxes obtained by Fischer-Tropsch synthesis, fatty acid esters and glycerides, and silicone waxes such as derivatives of poly(di)methylsiloxane. In one embodiment, the at least one wax may be present in the composition up to 3%, and in another embodiment at least 3%, such as up to 30% or up to 50%.

As described above, the composition may also comprise at least one liquid fatty phase wherein the liquid fatty phase comprises at least one structuring polymer and at least one oil-soluble polymer chosen from alkyl celluloses and alkylated guar gums. In one embodiment, the liquid fatty phase may further comprise additional ingredients chosen from at least one fatty alcohol.

The composition of the present invention, in one embodiment, may comprise a physiologically acceptable medium. The composition may also further comprise at least one suitable additive commonly used in the field concerned chosen from coloring agents, antioxidants, essential oils, preserving agents, fragrances, neutralizing agents, liposoluble polymers, and cosmetically active agents and dermatological active agents such as, for example, emollients, moisturizers, vitamins, essential fatty acids and sunscreens. The at least one additive is generally present in a concentration ranging from 0% to 20% by weight of the total weight of the composition, such as from 0% to 10%.

Needless to say, the person skilled in the art will take care to select the optional additional additives and the amount thereof such that at least one advantageous property of the composition according to the invention, such as stability, is not, or is not substantially, adversely affected by the addition(s) envisaged.

The compositions of the invention may also comprise at least one coloring agent chosen from pigments, dyes, nacres, and pearling agents. The at least one coloring agent may be chosen, for example, in order to obtain make-up compositions which give good coverage, that is, which do not leave a significant amount of the at least one keratin material to which it is applied showing through. The pigments may also reduce the sticky feel of the compositions, unlike soluble dyes.

Representative liposoluble dyes which may be used according to the present invention include Sudan red, DC Red 17, DC Green 6, β-carotene, soybean oil, Sudan brown, DC Yellow 11, DC Violet 2, DC Orange 5, quinoline yellow, and annatto. The liposoluble dyes, when present, generally have a concentration ranging up to 20% by weight of the total weight of the composition, such as from 0.1% to 6%.

The pigments which may be used according to the present invention may be chosen from white, colored, mineral, organic, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate and ferric blue. Representative examples of organic pigments include carbon black, pigments of D & C type, and lakes based on cochineal carmine, barium, strontium, calcium and aluminum. If present, the pigments may have a concentration ranging up to 40% by weight of the total weight of the composition, such as from 1% to 35%, and further such as from 2% to 25%.

The nacreous pigments (or nacres) which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacres, if present, may have a concentration ranging up to 30% by weight of the total weight of the composition, such as from 0.1% to 20%.

The packaging and application device for any subject of the invention may be chosen and manufactured by persons skilled in the art on the basis of their general knowledge, and adapted according to the nature of the composition to be packaged. Indeed, the type of device to be used may be in particular linked to the consistency of the composition, in particular to its viscosity; it may also depend on the nature of the constituents present in the composition, such as the presence of volatile compounds.

The invention will be illustrated by, but is not intended to be limited to, the following examples.

EXAMPLE 1

Clear Anhydrous Sunscreen Stick

TABLE 1

| RAW MATERIALS | Phase | A | B | C | D | E |
|---|---|---|---|---|---|---|
| Schercemol DISM (Diisostearyl malate) | A | 10 | 10 | 10 | 10 | 10 |
| Ceraphyl 45 (Dioctyl malate) | A | 10 | 10 | 20 | 20 | 20 |
| Cristal 0 (Castor oil) | A | 33 | 32.95 | 30.6 | 29.9 | 29 |
| NatureChem PGR (Propylene glycol ricinoleate) | A | 10.5 | 10.5 | 10.5 | 10.5 | 10.5 |
| Macromelt 6212 (Polyamide resin) | B | 16 | 16 | 16 | 16 | 16 |
| Cetyl Alcohol | C | — | — | 2 | 3 | 4 |
| Others*₁ | E | — | 0.05 | 0.4 | 0.1 | — |
| Uvinul M40 USP (Benzophenone-3) | D | 3 | 3 | 3 | 3 | 3 |
| Parsol MCX (Octyl methoxy cinnamate) | D | 7.5 | 7.5 | 7.5 | 7.5 | 7.5 |

Others*₁: Preservatives, masking agents, colorants, vitamins, oil-soluble actives, anti-oxidants, and dermatological actives.

The compositions of table 1 were prepared using the following procedure. The ingredients of phase A were added to a main vessel and heated to 110-115° C. while mixing with the aid of an impeller mixer. At 110-115° C. phase B was added to phase A with continued mixing. The beads of polyamide resin were allowed to dissolve and the mixture was removed from the heat and cooled to 80-82° C. Phases C, D, and E were added to the AB mixture while maintaining the temperature at about 80-82° C. with slow impeller mixing. The compositions were mixed until homogeneous (about 1 minute), then used to fill a suitable container or mold.

The resulting compositions were firm at room temperature. A very fine uniform oil coat covered the surface of some of the compositions, however, none of the compositions failed the stability test. At elevated temperatures (45° C.), the overall structure and stick characteristics remained unchanged. There was a moderate oil coat on the surface of the stick structure of some of the compositions, however, none of the compositions failed the stability test.

EXAMPLE 2

Clear Anhydrous Sunscreen Stick with an Oil-Soluble Cationic Polymer

TABLE 2

| RAW MATERIALS | Phase | A | B | C |
|---|---|---|---|---|
| Schercemol DISM (Diisostearyl malate) | A | 10 | 10 | 10 |
| Ceraphyl 45 (Dioctyl malate) | A | 20 | 200 | 20 |
| Cristal 0 (Castor Oil) | A | 28.9 | 27.9 | 29.4 |
| NatureChem PGR (Propylene glycol ricinoleate) | A | 10.5 | 10.5 | 10.5 |
| Glucquat-100 (Lauryl methyl gluceth-10 hydroxypropyl dimmonium chloride) | A | 1 | 2 | 0.5 |
| Macromelt 6212 (Polyamide resin) | B | 16 | 16 | 16 |
| Cetyl Alcohol | C | 3 | 3 | 3 |
| Propyl Paraben | C | 0.1 | 0.1 | 0.1 |
| Uvinul M40 USP (Benzophenone-3) | D | 3 | 3 | 3 |
| Parsol MCX (Octyl methoxy cinnamate) | D | 7.5 | 7.5 | 7.5 |

The compositions of table 2 were prepared using the following procedure. The ingredients of phase A were added to a main vessel and heated to 110-115° C. while mixing with the aid of an impeller mixer. At 110-115° C. phase B was added to phase A with continued mixing. The beads of polyamide resin were allowed to dissolve and the mixture was removed from the heat and cooled to 80-82° C. Phases C, and D were added to the AB mixture while maintaining the temperature at about 80-82° C. with slow impeller mixing. The compositions were mixed until homogeneous (about 1 minute), then used to fill a suitable container or mold.

The resulting compositions were firm at room temperature. A very fine uniform oil coat covered the surface of some of the compositions, however, none of the compositions failed the stability test. At elevated temperatures (45° C.), the overall structure and stick characteristics remained unchanged. There was a moderate oil coat on the surface of the stick structure of some of the compositions, however, none of the compositions failed the stability test.

EXAMPLE 3

Clear Anhydrous Sunscreen Sticks with an Oil-Soluble Cationic Polymer

TABLE 3

| RAW MATERIALS | Phase | A | B | C | D | E |
|---|---|---|---|---|---|---|
| Schercemol DISM (Diisostearyl malate) | A | 10 | 10 | 10 | 10 | 10 |
| Ceraphyl 45 (Dioctyl malate) | A | 20 | 20 | 20 | 20 | 20 |
| Cristal 0 (Caster Oil) | A | 26.15 | 24.15 | 22.9 | 23.9 | 23.15 |
| NatureChem PGR (Propylene glycol ricinoleate) | A | 10.5 | 10.5 | 10.5 | 10.5 | 10.5 |
| Macromelt 6212 (Polyamide resin) | B | 16 | 16 | 16 | 16 | 16 |
| N-Hance-AG-50 ($C_1$-$C_5$ alkyl galactomannan) | A | — | 2 | — | — | — |
| N-Hance-AG-200 ($C_1$-$C_5$ alkyl galactomannan) | A | — | — | 3 | — | — |
| Ethocel 100 (Ethyl cellulose) | A | — | — | — | 2 | — |
| Ethocel 7 (Ethyl cellulose) | A | — | — | — | — | 3 |
| Cetyl Alcohol | C | 4 | 4 | 4 | 4 | 4 |
| Propyl Paraben | C | 0.1 | 0.1 | 0.1 | 0.1 | 0.1 |
| Parsol 1789 (Butyl methoxydibenzol methane) | D | 3 | 3 | 3 | 3 | 3 |
| Neo Heliopan 303 (Octocrylene) | D | 10 | 10 | 10 | 10 | 10 |
| Flavoring Oil | E | 0.25 | 0.25 | 0.5 | 0.5 | 0.25 |

The compositions of table 3 were prepared using the following procedure. The ingredients of phase A were added to a main vessel and heated to 110-115° C. while mixing with the aid of an impeller mixer. At 110-115° C. phase B was added to phase A with continued mixing. The beads of polyamide resin were allowed to dissolve and the mixture was removed from the heat and cooled to 80-82° C. Phases C, D, and E were added to the AB mixture while maintaining the temperature at about 80-82° C. with slow impeller mixing. The compositions were mixed until homogeneous (about 1 minute), then used to fill a suitable container or mold.

The resulting compositions were firm at room temperature. A very fine uniform oil coat covered the surface of some of the compositions, however, none of the compositions failed the stability test. At elevated temperatures (45° C.), the overall structure and stick characteristics remained unchanged. There was a moderate oil coat on the surface of the stick structure, however, none of the compositions failed the stability test.

We claim:

1. A composition comprising at least one liquid fatty phase which comprises:
   (i) at least one structuring polymer, wherein said at least one structuring polymer is chosen from the group consisting of ethylenediamine/stearyl dimer tallate copolymer and ethylenediamine/stearyl dimmer dilinoleate copolymer; and
   (ii) at least one oil-soluble polymer chosen from alkyl celluloses and alkylated guar gums.

2. The composition according to claim 1, wherein said at least one liquid fatty phase of the composition comprises at least one oil.

3. The composition according to claim 2, wherein said at least one oil is chosen from at least one polar oil and at least one apolar oil.

4. The composition according to claim 3, wherein said at least one polar oil is chosen from:
- hydrocarbon-based plant oils with a high content of triglycerides comprising fatty acid esters of glycerol in which the fatty acids comprise chains having from 4 to 24 carbon atoms, said chains possibly being chosen from linear and branched, and saturated and unsaturated chains;
- synthetic oils or esters of formula $R_5COOR_6$ in which $R_5$ is chosen from linear and branched fatty acid residues comprising from 1 to 40 carbon atoms and $R_5+R_6 \geq 10$;
- synthetic ethers containing from 10 to 40 carbon atoms;
- $C_8$ to $C_{26}$ fatty alcohols; and
- $C_8$ to $C_{26}$ fatty acids.

5. The composition according to claim 3, wherein said at least one apolar oil is chosen from:
- silicone oils chosen from volatile and non-volatile, linear and cyclic polydimethylsiloxanes that are liquid at room temperature;
- polydimethylsiloxanes comprising alkyl or alkoxy groups which are pendant and/or at the end of the silicone chain, the groups each containing from 2 to 24 carbon atoms;
- phenylsilicones; and
- hydrocarbons chosen from linear and branched, volatile and non-volatile hydrocarbons of synthetic and mineral origin.

6. The composition according to claim 1, wherein said at least one liquid fatty phase comprises at least one non-volatile oil.

7. The composition according to claim 6, wherein said at least one non-volatile oil is chosen from hydrocarbon-based oils of mineral, plant and synthetic origin, synthetic esters and ethers, and silicone oils.

8. The composition according to claim 1, wherein said at least one liquid fatty phase comprises at least one volatile solvent chosen from hydrocarbon-based solvents and silicone solvents optionally comprising alkyl or alkoxy groups that are pendant or at the end of a silicone chain.

9. The composition according to claim 1, wherein said alkyl celluloses are chosen from ethylcelluloses.

10. The composition according to claim 1, wherein said alkylated guar gums are chosen from $C_1$-$C_5$ alkyl galactomannans.

11. The composition according to claim 1, wherein said alkylated guar gums are chosen from ethyl guars.

12. The composition according to claim 1, wherein said at least one liquid fatty phase further comprises a silicone oil.

13. The composition according to claim 1, further comprising at least one fatty alcohol.

14. A composition according to claim 1, further comprising at least one oil-soluble ester.

15. The composition according to claim 14 wherein the at least one oil-soluble ester comprises at least one free hydroxy group.

16. The composition according to claim 14 wherein the at least one oil-soluble ester is not castor oil.

* * * * *

UNITED STATES PATENT AND TRADEMARK OFFICE
CERTIFICATE OF CORRECTION

PATENT NO.        : 7,276,547 B2                                               Page 1 of 1
APPLICATION NO. : 09/733896
DATED             : October 2, 2007
INVENTOR(S)       : Carlos Pinzon et al.

It is certified that error appears in the above-identified patent and that said Letters Patent is hereby corrected as shown below:

Title page, item (54), line 3, "POLYMERS" should read --POLYMER--.

Claim 1, column 20., line 61, "dimmer" should read --dimer--.

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,276,547 B2 | Page 1 of 1 |
| APPLICATION NO. | : 09/733896 | |
| DATED | : October 2, 2007 | |
| INVENTOR(S) | : Carlos Pinzon et al. | |

It is certified that error appears in the above-identified patent and that said Letters Patent is hereby corrected as shown below:

Title page, item (54), line 3 and Column 1 line 3, "POLYMERS" should read --POLYMER--.

Claim 1, column 20., line 61, "dimmer" should read --dimer--.

This certificate supersedes the Certificate of Correction issued March 4, 2008.

Signed and Sealed this

First Day of April, 2008

JON W. DUDAS
*Director of the United States Patent and Trademark Office*